United States Patent
Inouye et al.

(10) Patent No.: US 8,853,374 B2
(45) Date of Patent: Oct. 7, 2014

(54) PROCESS FOR PRODUCTION OF RECOMBINANT PROTEINS AS A SOLUBLE FORM

(75) Inventors: Satoshi Inouye, Yokohama (JP); Yuiko Sahara, Yokohama (JP)

(73) Assignee: JNC Corporation, Tokyo (JP)

( * ) Notice: Subject to any disclaimer, the term of this patent is extended or adjusted under 35 U.S.C. 154(b) by 1174 days.

(21) Appl. No.: 11/902,030

(22) Filed: Sep. 18, 2007

(65) Prior Publication Data

US 2008/0076156 A1    Mar. 27, 2008

(30) Foreign Application Priority Data

Sep. 19, 2006  (JP) ................ 2006-253045

(51) Int. Cl.
C07H 21/02    (2006.01)
C12P 21/06    (2006.01)
C12N 15/62    (2006.01)

(52) U.S. Cl.
CPC .................................. C12N 15/62 (2013.01)
USPC ...................................... 536/23.1; 435/69.1

(58) Field of Classification Search
None
See application file for complete search history.

(56) References Cited

U.S. PATENT DOCUMENTS 6,544,754 B2 *  4/2003  Inouye ............................. 435/8

FOREIGN PATENT DOCUMENTS

| EP | 0 230 869 A2 | 8/1987 | | |
| EP | 0372352 A2 | 6/1990 | | |
| GB | 2441208 A | 2/2008 | | |
| SE | WO/92/07868 | * | 5/1992 | ............ C07K 1/107 |
| WO | WO 03/093321 A1 | 11/2003 | | |
| WO | WO 2005/033132 A3 | 4/2005 | | |

OTHER PUBLICATIONS

Kunesel et al., Identification of Novel Protein-Protein Interaction Using a Versatile Mammalian Tandem Affinity Purification Expression System., Genome Research, 2002, vol. 12, pp. 487-492.*
Doi et al., Novel Fluorescence Labeling and High-Throughput Assay Technologies for In Vitro Analysis of Protein Interactions., Genome Research, 2002, vol. 12, pp. 487-492.*
Kim et al., Proteome response of *Escherichia coli* fed-batch culture to temperature downshift., Appl Microbiol Biotechnol, Mar. 18, 2005, vol. 68, pp. 786-793.*
Andersson et al., Improved systems for hydrophobig tagging of recombinant immunogens for efficient iscom incorporation., Journal of Immunological Methods, 2000, vol. 238, pp. 181-193.*
Tannous et al. (Codon-Optimized Gaussia Luciferase cDNA for Mammalian Gene Expression in Culture and in Vivo., Molecular Therapy (E. pub. Dec. 2004) vol. 11, pp. 435-443.*
Inouye et al., Cloning and sequence analysis of cDNA for the luminescent protein aequorin, Proc Natl Acad Sci U S A. (May 1985) vol. 82(10): pp. 3154-3158.*
United Kingdom Search Report dated Jan. 15, 2008 relating to GB 0718095.3.

(Continued)

Primary Examiner — Alexander Kim
(74) Attorney, Agent, or Firm — Hogan Lovells US LLP

(57) ABSTRACT

A target protein is prepared as soluble protein using a recombinant protein expression system. An expression vector is used that includes (1) an expression-inducible promoter sequence; (2) a first coding sequence including a polynucleotide coding for a polypeptide that is represented by the formula $(Z)_n$; and (3) a second coding sequence that includes a polynucleotide that codes for a target protein. A method of producing the target protein is also used that includes expressing protein using this expression vector.

29 Claims, 7 Drawing Sheets

(56) References Cited

OTHER PUBLICATIONS

Biosci. Biotech. Biochem., vol. 57, 1993, Matsumoto, T. et al., "Construction of Sandwich Enzyme Immunoassay for Rat Transthyretin Using Recombinant Antigen Approach, and Its Application," pp. 414-418.
Applied and Environmental Microbiology, vol. 70, Mar. 2004, Vollenkle, C. et al., "Construction of a Functional S-Layer Fusion Protein Comprising an Immunoglobulin G-Binding Domain for Development of Specific Adsorbents for Extracorporeal Blood Purification," pp. 1514-1521.
Applied and Environmental Microbiology, vol. 72, Nov. 2006, Brockelbank, J. A. et al., "Recombinant *Escherichia coli* Strain Produces a ZZ Domain Displaying Biopolyester Granules Suitable for Immunoglobulin G Purification," 7394-7397.
Journal of Immunological Methods, vol. 321, 2007, Mazor, Y. et al., "Antibody Internalization Studied Using a Novel IgG Binding Toxin Fusion," pp. 41-59.
Biochemical and Biophysical Research Communications, vol. 213, Aug. 4, 1995, Griko, Y. V. et al., "Purification and Characterization of Human Pancreatic Polypeptide Expressed in *E. coli*," pp. 239-248.
Biochemical and Biophysical Research Communications, vol. 219, 1996, Frank, L. A. et al., "Use of proZZ-obelin Fusion Protein in Bioluminescent Immunoassay," pp. 475-479.
Qing et al., Jul. 2004, "Cold-shock induced high-yield protein production in *Escherichia coli*," Nature Biotechnology, vol. 22, No. 7, pp. 877-882.
Notice of Reasons for Rejection issued for the corresponding JP Application No. 2007-237784 on Jun. 5, 2012.
Notice of Reasons for Rejection issued for the corresponding JP Application No. 2007-237784 on Apr. 9, 2013.
Sagawa et al., (2005) "Kagaku to Seibutsu," Chemistry and Biology, 43(4), pp. 267-271.
Office Action issued for the corresponding GB Application No. GB0718095.3 on Jul. 29, 2010.
Office Action issued for the corresponding GB Application No. GB0718095.3 on Dec. 15, 2010.
Samuelsson, E. et al., 1991, "Facilitated In Vitro Refolding of Human Recombinant Insulin-like Growth Factor I Using a Solubilizing Fusion Partner," Biotechnology, V 9, 363-366.
Moks, T. et al., 1987, Expression of Human Insulin-like Growth Factor I in Bacteria: Use of Optimized Gene Fusion Vectors to Facilitate Protein Purification, Biochemistry, 26, 5239-5344.
Samuelsson, E. et al., 1994, Enhanced In Vitro Refolding of Insulin-like Growth Factor I Using a Solubilizing Fusion Partner, Biochemistry, 33, 4207-4211.
"Current Protocols in Molecular Biology," vol. 2, pp. 16.01-16.13.7, 1996.
Fox, Jeffrey D. et al., "Maltose-Binding Protein as a Solubility Enhancer," Methods in Molecular Biology, vol. 205, *E. coli* Gene Expression Protocols, pp. 99-117, (2003).
Nilsson, Björn et al., "A Synthetic IgG-Binding Domain Based on Staphylococcal Protein A," Protein Engineering, vol. 1, No. 2, pp. 107-113, 1987.

\* cited by examiner

SEQUENCE LISTING

```
<160> NUMBER OF SEQ ID NOS: 42

<210> SEQ ID NO 1
<211> LENGTH: 58
<212> TYPE: PRT
<213> ORGANISM: Artificial
<220> FEATURE:
<223> OTHER INFORMATION: Synthetic Construct

<400> SEQUENCE: 1

Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys Val
    50                  55

<210> SEQ ID NO 2
<211> LENGTH: 174
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(174)

<400> SEQUENCE: 2 gac aac aaa ttc aac aaa gaa caa caa aac gcg ttc tat gag atc tta        48
Asp Asn Lys Phe Asn Lys Glu Gln Gln Asn Ala Phe Tyr Glu Ile Leu
1               5                   10                  15 cat tta cct aac tta aac gaa gaa caa cga aac gcc ttc atc caa agt        96
His Leu Pro Asn Leu Asn Glu Glu Gln Arg Asn Ala Phe Ile Gln Ser
            20                  25                  30 tta aaa gat gac cca agc caa agc gct aac ctt tta gca gaa gct aaa       144
Leu Lys Asp Asp Pro Ser Gln Ser Ala Asn Leu Leu Ala Glu Ala Lys
        35                  40                  45 aag cta aat gat gct cag gcg ccg aaa gta                               174
Lys Leu Asn Asp Ala Gln Ala Pro Lys Val
    50                  55
```

<210> SEQ ID NO 3
<211> LENGTH: 116
<212> TYPE: PRT
<213> ORGANISM: Artificial
<220> FEATURE:
<223> OTHER INFORMATION: Synthetic Construct

<400> SEQUENCE: 3

```
Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys Val Asp Asn Lys Phe Asn Lys
50                  55                  60

Glu Gln Gln Asn Ala Phe Tyr Glu Ile Leu His Leu Pro Asn Leu Asn
65                  70                  75                  80

Glu Glu Gln Arg Asn Ala Phe Ile Gln Ser Leu Lys Asp Asp Pro Ser
                85                  90                  95

Gln Ser Ala Asn Leu Leu Ala Glu Ala Lys Lys Leu Asn Asp Ala Gln
            100                 105                 110

Ala Pro Lys Val
        115
```

<210> SEQ ID NO 4
<211> LENGTH: 348
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(348)

<400> SEQUENCE: 4

```
gac aac aaa ttc aac aaa gaa caa caa aac gcg ttc tat gag atc tta      48
Asp Asn Lys Phe Asn Lys Glu Gln Gln Asn Ala Phe Tyr Glu Ile Leu
1               5                   10                  15 cat tta cct aac tta aac gaa gaa caa cga aac gcc ttc atc caa agt      96
His Leu Pro Asn Leu Asn Glu Glu Gln Arg Asn Ala Phe Ile Gln Ser
            20                  25                  30 tta aaa gat gac cca agc caa agc gct aac ctt tta gca gaa gct aaa     144
Leu Lys Asp Asp Pro Ser Gln Ser Ala Asn Leu Leu Ala Glu Ala Lys
        35                  40                  45 aag cta aat gat gct cag gcg ccg aaa gta gac aac aaa ttc aac aaa     192
Lys Leu Asn Asp Ala Gln Ala Pro Lys Val Asp Asn Lys Phe Asn Lys
50                  55                  60 gaa caa caa aac gcg ttc tat gag atc tta cat tta cct aac tta aac     240
Glu Gln Gln Asn Ala Phe Tyr Glu Ile Leu His Leu Pro Asn Leu Asn
65                  70                  75                  80 gaa gaa caa cga aac gcc ttc atc caa agt tta aaa gat gac cca agc     288
Glu Glu Gln Arg Asn Ala Phe Ile Gln Ser Leu Lys Asp Asp Pro Ser
                85                  90                  95 caa agc gct aac ctt tta gca gaa gct aaa aag cta aat gat gct cag     336
Gln Ser Ala Asn Leu Leu Ala Glu Ala Lys Lys Leu Asn Asp Ala Gln
            100                 105                 110 gcg ccg aaa gta                                                     348
Ala Pro Lys Val
```

-continued

115

<210> SEQ ID NO 5
<211> LENGTH: 211
<212> TYPE: PRT
<213> ORGANISM: Artificial
<220> FEATURE:
<223> OTHER INFORMATION: Synthetic Construct

<400> SEQUENCE: 5

```
Met Asn His Lys Val His His His His His Met Glu Leu Gly Thr
1               5                   10                  15

Leu Glu Gly Ser Glu Ser Met Lys Leu Thr Ser Asp Phe Asp Asn Pro
            20                  25                  30

Arg Trp Ile Gly Arg His Lys His Met Phe Asn Phe Leu Asp Val Asn
        35                  40                  45

His Asn Gly Lys Ile Ser Leu Asp Glu Met Val Tyr Lys Ala Ser Asp
    50                  55                  60

Ile Val Ile Asn Asn Leu Gly Ala Thr Pro Glu Gln Ala Lys Arg His
65                  70                  75                  80

Lys Asp Ala Val Glu Ala Phe Phe Gly Gly Ala Gly Met Lys Tyr Gly
                85                  90                  95

Val Glu Thr Asp Trp Pro Ala Tyr Ile Glu Gly Trp Lys Lys Leu Ala
            100                 105                 110

Thr Asp Glu Leu Glu Lys Tyr Ala Lys Asn Glu Pro Thr Leu Ile Arg
        115                 120                 125

Ile Trp Gly Asp Ala Leu Phe Asp Ile Val Asp Lys Asp Gln Asn Gly
    130                 135                 140

Ala Ile Thr Leu Asp Glu Trp Lys Ala Tyr Thr Lys Ala Ala Gly Ile
145                 150                 155                 160

Ile Gln Ser Ser Glu Asp Cys Glu Glu Thr Phe Arg Val Cys Asp Ile
                165                 170                 175

Asp Glu Ser Gly Gln Leu Asp Val Asp Glu Met Thr Arg Gln His Leu
            180                 185                 190

Gly Phe Trp Tyr Thr Met Asp Pro Ala Cys Glu Lys Leu Tyr Gly Gly
        195                 200                 205

Ala Val Pro
    210
```

<210> SEQ ID NO 6
<211> LENGTH: 636
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(636)

<400> SEQUENCE: 6

```
atg aat cac aaa gtg cat cat cat cat cat cat atg gag ctc ggt acc        48
Met Asn His Lys Val His His His His His His Met Glu Leu Gly Thr
1               5                   10                  15 ctc gag gga tcc gaa tcc atg aaa ctt aca tca gac ttc gac aac cca        96
Leu Glu Gly Ser Glu Ser Met Lys Leu Thr Ser Asp Phe Asp Asn Pro
            20                  25                  30 aga tgg att gga cga cac aag cac atg ttc aat ttc ctt gat gtc aac       144
Arg Trp Ile Gly Arg His Lys His Met Phe Asn Phe Leu Asp Val Asn
        35                  40                  45
```

```
cac aat gga aaa atc tct ctt gac gag atg gtc tac aag gca tct gat      192
His Asn Gly Lys Ile Ser Leu Asp Glu Met Val Tyr Lys Ala Ser Asp
     50                  55                  60 att gtc atc aat aac ctt gga gca aca cct gag caa gcc aaa cga cac      240
Ile Val Ile Asn Asn Leu Gly Ala Thr Pro Glu Gln Ala Lys Arg His
 65                  70                  75                  80 aaa gat gct gta gaa gcc ttc ttc gga gga gct gga atg aaa tat ggt      288
Lys Asp Ala Val Glu Ala Phe Phe Gly Gly Ala Gly Met Lys Tyr Gly
                 85                  90                  95 gtg gaa act gat tgg cct gca tat att gaa gga tgg aaa aaa ttg gct      336
Val Glu Thr Asp Trp Pro Ala Tyr Ile Glu Gly Trp Lys Lys Leu Ala
            100                 105                 110 act gat gaa ttg gag aaa tac gcc aaa aac gaa cca acg ctc atc cgt      384
Thr Asp Glu Leu Glu Lys Tyr Ala Lys Asn Glu Pro Thr Leu Ile Arg
        115                 120                 125 ata tgg ggt gat gct ttg ttt gat atc gtt gac aaa gat caa aat gga      432
Ile Trp Gly Asp Ala Leu Phe Asp Ile Val Asp Lys Asp Gln Asn Gly
    130                 135                 140 gcc att aca ctg gat gaa tgg aaa gca tac acc aaa gct gct ggt atc      480
Ala Ile Thr Leu Asp Glu Trp Lys Ala Tyr Thr Lys Ala Ala Gly Ile
145                 150                 155                 160 atc caa tca tca gaa gat tgc gag gaa aca ttc aga gtg tgc gat att      528
Ile Gln Ser Ser Glu Asp Cys Glu Glu Thr Phe Arg Val Cys Asp Ile
                165                 170                 175 gat gaa agt gga caa ctc gat gtt gat gag atg aca aga caa cat tta      576
Asp Glu Ser Gly Gln Leu Asp Val Asp Glu Met Thr Arg Gln His Leu
            180                 185                 190 gga ttt tgg tac act atg gac cct gct tgc gaa aag ctc tac ggt gga      624
Gly Phe Trp Tyr Thr Met Asp Pro Ala Cys Glu Lys Leu Tyr Gly Gly
        195                 200                 205 gct gtc ccc taa                                                      636
Ala Val Pro
    210

<210> SEQ ID NO 7
<211> LENGTH: 334
<212> TYPE: PRT
<213> ORGANISM: Artificial
<220> FEATURE:
<223> OTHER INFORMATION: Synthetic Construct

<400> SEQUENCE: 7

Met Asn His Lys Val His His His His His Met Ala Gln His Asp
 1               5                  10                  15

Glu Ala Val Asp Asn Lys Phe Asn Lys Glu Gln Gln Asn Ala Phe Tyr
                 20                  25                  30

Glu Ile Leu His Leu Pro Asn Leu Asn Glu Glu Gln Arg Asn Ala Phe
             35                  40                  45

Ile Gln Ser Leu Lys Asp Asp Pro Ser Gln Ser Ala Asn Leu Leu Ala
         50                  55                  60

Glu Ala Lys Lys Leu Asn Asp Ala Gln Ala Pro Lys Val Asp Asn Lys
 65                  70                  75                  80

Phe Asn Lys Glu Gln Gln Asn Ala Phe Tyr Glu Ile Leu His Leu Pro
                 85                  90                  95

Asn Leu Asn Glu Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125
```

```
Asp Ala Gln Ala Pro Lys Val Asp Ala Asn Ser Ser Gly Ser Glu
    130                 135                 140

Phe Met Lys Leu Thr Ser Asp Phe Asp Asn Pro Arg Trp Ile Gly Arg
145                 150                 155                 160

His Lys His Met Phe Asn Phe Leu Asp Val Asn His Asn Gly Lys Ile
                165                 170                 175

Ser Leu Asp Glu Met Val Tyr Lys Ala Ser Asp Ile Val Ile Asn Asn
            180                 185                 190

Leu Gly Ala Thr Pro Glu Gln Ala Lys Arg His Lys Asp Ala Val Glu
        195                 200                 205

Ala Phe Phe Gly Gly Ala Gly Met Lys Tyr Gly Val Glu Thr Asp Trp
    210                 215                 220

Pro Ala Tyr Ile Glu Gly Trp Lys Lys Leu Ala Thr Asp Glu Leu Glu
225                 230                 235                 240

Lys Tyr Ala Lys Asn Glu Pro Thr Leu Ile Arg Ile Trp Gly Asp Ala
                245                 250                 255

Leu Phe Asn Ile Val Asp Lys Asp Gln Asn Gly Ala Ile Thr Leu Asp
            260                 265                 270

Glu Trp Lys Ala Tyr Thr Lys Ala Ala Gly Ile Ile Gln Ser Ser Glu
        275                 280                 285

Asp Cys Glu Glu Thr Phe Arg Val Cys Asp Ile Asp Glu Ser Gly Gln
    290                 295                 300

Leu Asp Val Asp Glu Met Thr Arg Gln His Leu Gly Phe Trp Tyr Thr
305                 310                 315                 320

Met Asp Pro Ala Cys Glu Lys Leu Tyr Gly Gly Ala Val Pro
                325                 330

<210> SEQ ID NO 8
<211> LENGTH: 1005
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(1005)

<400> SEQUENCE: 8 atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
                20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
            35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
        50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
Asn Leu Asn Glu Glu Gln Arg Asn Ala Phe Ile Gln Ser Leu Lys Asp
```

```
gac cca agc caa agc gct aac ctt tta gca gaa gct aaa aag cta aat    384
Asp Pro Ser Gln Ser Ala Asn Leu Leu Ala Glu Ala Lys Lys Leu Asn
            115                 120                 125 gat gct cag gcg ccg aaa gta gac gca aat tcg agc tcg gga tcc gaa    432
Asp Ala Gln Ala Pro Lys Val Asp Ala Asn Ser Ser Ser Gly Ser Glu
130                 135                 140 ttc atg aaa ctt aca tca gac ttc gac aac cca aga tgg att gga cga    480
Phe Met Lys Leu Thr Ser Asp Phe Asp Asn Pro Arg Trp Ile Gly Arg
145                 150                 155                 160 cac aag cac atg ttc aat ttc ctt gat gtc aac cac aat gga aaa atc    528
His Lys His Met Phe Asn Phe Leu Asp Val Asn His Asn Gly Lys Ile
                165                 170                 175 tct ctt gac gag atg gtc tac aag gca tct gat att gtc atc aat aac    576
Ser Leu Asp Glu Met Val Tyr Lys Ala Ser Asp Ile Val Ile Asn Asn
            180                 185                 190 ctt gga gca aca cct gag caa gcc aaa cga cac aaa gat gct gta gaa    624
Leu Gly Ala Thr Pro Glu Gln Ala Lys Arg His Lys Asp Ala Val Glu
        195                 200                 205 gcc ttc ttc gga gga gct gga atg aaa tat ggt gtg gaa act gat tgg    672
Ala Phe Phe Gly Gly Ala Gly Met Lys Tyr Gly Val Glu Thr Asp Trp
    210                 215                 220 cct gca tat att gaa gga tgg aaa aaa ttg gct act gat gaa ttg gag    720
Pro Ala Tyr Ile Glu Gly Trp Lys Lys Leu Ala Thr Asp Glu Leu Glu
225                 230                 235                 240 aaa tac gcc aaa aac gaa cca acg ctc atc cgt ata tgg ggt gat gct    768
Lys Tyr Ala Lys Asn Glu Pro Thr Leu Ile Arg Ile Trp Gly Asp Ala
                245                 250                 255 ttg ttt aat atc gtt gac aaa gat caa aat gga gcc att aca ctg gat    816
Leu Phe Asn Ile Val Asp Lys Asp Gln Asn Gly Ala Ile Thr Leu Asp
            260                 265                 270 gaa tgg aaa gca tac acc aaa gct gct ggt atc atc caa tca tca gaa    864
Glu Trp Lys Ala Tyr Thr Lys Ala Ala Gly Ile Ile Gln Ser Ser Glu
        275                 280                 285 gat tgc gag gaa aca ttc aga gtg tgc gat att gat gaa agt gga caa    912
Asp Cys Glu Glu Thr Phe Arg Val Cys Asp Ile Asp Glu Ser Gly Gln
    290                 295                 300 ctc gat gtt gat gag atg aca aga caa cat tta gga ttt tgg tac act    960
Leu Asp Val Asp Glu Met Thr Arg Gln His Leu Gly Phe Trp Tyr Thr
305                 310                 315                 320 atg gac cct gct tgc gaa aag ctc tac ggt gga gct gtc ccc taa       1005
Met Asp Pro Ala Cys Glu Lys Leu Tyr Gly Gly Ala Val Pro
                325                 330
```

<210> SEQ ID NO 9
<211> LENGTH: 182
<212> TYPE: PRT
<213> ORGANISM: Artificial
<220> FEATURE:
<223> OTHER INFORMATION: Synthetic Construct

<400> SEQUENCE: 9

```
Met Asn His Lys Val His His His His His Met Glu Leu Lys Pro
1               5                   10                  15

Thr Glu Asn Asn Glu Asp Phe Asn Ile Val Ala Val Ala Ser Asn Phe
                20                  25                  30

Ala Thr Thr Asp Leu Asp Ala Asp Arg Gly Lys Leu Pro Gly Lys Lys
            35                  40                  45

Leu Pro Leu Glu Val Leu Lys Glu Met Glu Ala Asn Ala Arg Lys Ala
        50                  55                  60
```

```
Gly Cys Thr Arg Gly Cys Leu Ile Cys Leu Ser His Ile Lys Cys Thr
 65                  70                  75                  80

Pro Lys Met Lys Lys Phe Ile Pro Gly Arg Cys His Thr Tyr Glu Gly
                 85                  90                  95

Asp Lys Glu Ser Ala Gln Gly Gly Ile Gly Glu Ala Ile Val Asp Ile
            100                 105                 110

Pro Glu Ile Pro Gly Phe Lys Asp Leu Glu Pro Met Glu Gln Phe Ile
        115                 120                 125

Ala Gln Val Asp Leu Cys Val Asp Cys Thr Thr Gly Cys Leu Lys Gly
    130                 135                 140

Leu Ala Asn Val Gln Cys Ser Asp Leu Leu Lys Lys Trp Leu Pro Gln
145                 150                 155                 160

Arg Cys Ala Thr Phe Ala Ser Lys Ile Gln Gly Gln Val Asp Lys Ile
                165                 170                 175

Lys Gly Ala Gly Gly Asp
            180

<210> SEQ ID NO 10
<211> LENGTH: 549
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(549)

<400> SEQUENCE: 10 atg aat cac aaa gtg cat cat cat cat cat cat atg gag ctc aag ccc     48
Met Asn His Lys Val His His His His His His Met Glu Leu Lys Pro
  1               5                  10                  15 acc gag aac aac gaa gac ttc aac atc gtg gcc gtg gcc agc aac ttc     96
Thr Glu Asn Asn Glu Asp Phe Asn Ile Val Ala Val Ala Ser Asn Phe
             20                  25                  30 gcg acc acg gat ctc gat gct gac cgc ggg aag ttg ccc ggc aag aag    144
Ala Thr Thr Asp Leu Asp Ala Asp Arg Gly Lys Leu Pro Gly Lys Lys
         35                  40                  45 ctg ccg ctg gag gtg ctc aaa gag atg gaa gcc aat gcc cgg aaa gct    192
Leu Pro Leu Glu Val Leu Lys Glu Met Glu Ala Asn Ala Arg Lys Ala
     50                  55                  60 ggc tgc acc agg ggc tgt ctg atc tgc ctg tcc cac atc aag tgc acg    240
Gly Cys Thr Arg Gly Cys Leu Ile Cys Leu Ser His Ile Lys Cys Thr
 65                  70                  75                  80 ccc aag atg aag aag ttc atc cca gga cgc tgc cac acc tac gaa ggc    288
Pro Lys Met Lys Lys Phe Ile Pro Gly Arg Cys His Thr Tyr Glu Gly
                 85                  90                  95 gac aaa gag tcc gca cag ggc ggc ata ggc gag gcg atc gtc gac att    336
Asp Lys Glu Ser Ala Gln Gly Gly Ile Gly Glu Ala Ile Val Asp Ile
            100                 105                 110 cct gag att cct ggg ttc aag gac ttg gag ccc atg gag cag ttc atc    384
Pro Glu Ile Pro Gly Phe Lys Asp Leu Glu Pro Met Glu Gln Phe Ile
        115                 120                 125 gca cag gtc gat ctg tgt gtg gac tgc aca act ggc tgc ctc aaa ggg    432
Ala Gln Val Asp Leu Cys Val Asp Cys Thr Thr Gly Cys Leu Lys Gly
    130                 135                 140 ctt gcc aac gtg cag tgt tct gac ctg ctc aag aag tgg ctg ccg caa    480
Leu Ala Asn Val Gln Cys Ser Asp Leu Leu Lys Lys Trp Leu Pro Gln
145                 150                 155                 160
```

```
cgc tgt gcg acc ttt gcc agc aag atc cag ggc cag gtg gac aag atc    528
Arg Cys Ala Thr Phe Ala Ser Lys Ile Gln Gly Gln Val Asp Lys Ile
            165                 170                 175 aag ggg gcc ggt ggt gac taa                                        549
Lys Gly Ala Gly Gly Asp
            180
```

<210> SEQ ID NO 11
<211> LENGTH: 313
<212> TYPE: PRT
<213> ORGANISM: Artificial
<220> FEATURE:
<223> OTHER INFORMATION: Synthetic Construct

<400> SEQUENCE: 11

```
Met Asn His Lys Val His His His His His Met Ala Gln His Asp
1               5                   10                  15

Glu Ala Val Asp Asn Lys Phe Asn Lys Glu Gln Gln Asn Ala Phe Tyr
                20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
50                  55                  60

Glu Ala Lys Lys Leu Asn Asp Ala Gln Ala Pro Lys Val Asp Asn Lys
65                  70                  75                  80

Phe Asn Lys Glu Gln Gln Asn Ala Phe Tyr Glu Ile Leu His Leu Pro
                85                  90                  95

Asn Leu Asn Glu Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125

Asp Ala Gln Ala Pro Lys Val Asp Ala Asn Ser Ser Ser Gly Ser Glu
130                 135                 140

Phe Lys Pro Thr Glu Asn Asn Glu Asp Phe Asn Ile Val Ala Val Ala
145                 150                 155                 160

Ser Asn Phe Ala Thr Thr Asp Leu Asp Ala Asp Arg Gly Lys Leu Pro
                165                 170                 175

Gly Lys Lys Leu Pro Leu Glu Val Leu Lys Glu Met Glu Ala Asn Ala
            180                 185                 190

Arg Lys Ala Gly Cys Thr Arg Gly Cys Leu Ile Cys Leu Ser His Ile
        195                 200                 205

Lys Cys Thr Pro Lys Met Lys Lys Phe Ile Pro Gly Arg Cys His Thr
210                 215                 220

Tyr Glu Gly Asp Lys Glu Ser Ala Gln Gly Gly Ile Gly Glu Ala Ile
225                 230                 235                 240

Val Asp Ile Pro Glu Ile Pro Gly Phe Lys Asp Leu Glu Pro Met Glu
                245                 250                 255

Gln Phe Ile Ala Gln Val Asp Leu Cys Val Asp Cys Thr Thr Gly Cys
            260                 265                 270

Leu Lys Gly Leu Ala Asn Val Gln Cys Ser Asp Leu Leu Lys Lys Trp
        275                 280                 285

Leu Pro Gln Arg Cys Ala Thr Phe Ala Ser Lys Ile Gln Gly Gln Val
        290                 295                 300

Asp Lys Ile Lys Gly Ala Gly Gly Asp
305                 310
```

```
<210> SEQ ID NO 12
<211> LENGTH: 942
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(942)

<400> SEQUENCE: 12 atg aat cac aaa gtg cat cat cat cat cat cat atg gcg caa cac gat        48
Met Asn His Lys Val His His His His His His Met Ala Gln His Asp
1               5                   10                  15 gaa gcc gta gac aac aaa ttc aac aaa gaa caa caa aac gcg ttc tat        96
Glu Ala Val Asp Asn Lys Phe Asn Lys Glu Gln Gln Asn Ala Phe Tyr
            20                  25                  30 gag atc tta cat tta cct aac tta aac gaa gaa caa cga aac gcc ttc        144
Glu Ile Leu His Leu Pro Asn Leu Asn Glu Glu Gln Arg Asn Ala Phe
        35                  40                  45 atc caa agt tta aaa gat gac cca agc caa agc gct aac ctt tta gca        192
Ile Gln Ser Leu Lys Asp Asp Pro Ser Gln Ser Ala Asn Leu Leu Ala
    50                  55                  60 gaa gct aaa aag cta aat gat gct cag gcg ccg aaa gta gac aac aaa        240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct        288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat        336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat        384
Asp Pro Ser Gln Ser Ala Asn Leu Leu Ala Glu Ala Lys Lys Leu Asn
        115                 120                 125 gat gct cag gcg ccg aaa gta gac gca aat tcg agc tcg gga tcc gaa        432
Asp Ala Gln Ala Pro Lys Val Asp Ala Asn Ser Ser Ser Gly Ser Glu
    130                 135                 140 ttc aag ccc acc gag aac aac gaa gac ttc aac atc gtg gcc gtg gcc        480
Phe Lys Pro Thr Glu Asn Asn Glu Asp Phe Asn Ile Val Ala Val Ala
145                 150                 155                 160 agc aac ttc gcg acc acg gat ctc gat gct gac cgc ggg aag ttg ccc        528
Ser Asn Phe Ala Thr Thr Asp Leu Asp Ala Asp Arg Gly Lys Leu Pro
                165                 170                 175 ggc aag aag ctg ccg ctg gag gtg ctc aaa gag atg gaa gcc aat gcc        576
Gly Lys Lys Leu Pro Leu Glu Val Leu Lys Glu Met Glu Ala Asn Ala
            180                 185                 190 cgg aaa gct ggc tgc acc agg ggc tgt ctg atc tgc ctg tcc cac atc        624
Arg Lys Ala Gly Cys Thr Arg Gly Cys Leu Ile Cys Leu Ser His Ile
        195                 200                 205 aag tgc acg ccc aag atg aag aag ttc atc cca gga cgc tgc cac acc        672
Lys Cys Thr Pro Lys Met Lys Lys Phe Ile Pro Gly Arg Cys His Thr
    210                 215                 220 tac gaa ggc gac aaa gag tcc gca cag ggc ggc ata ggc gag gcg atc        720
Tyr Glu Gly Asp Lys Glu Ser Ala Gln Gly Gly Ile Gly Glu Ala Ile
225                 230                 235                 240 gtc gac att cct gag att cct ggg ttc aag gac ttg gag ccc atg gag        768
Val Asp Ile Pro Glu Ile Pro Gly Phe Lys Asp Leu Glu Pro Met Glu
                245                 250                 255 cag ttc atc gca cag gtc gat ctg tgt gtg gac tgc aca act ggc tgc        816
Gln Phe Ile Ala Gln Val Asp Leu Cys Val Asp Cys Thr Thr Gly Cys
```

```
                       260                 265                 270
ctc aaa ggg ctt gcc aac gtg cag tgt tct gac ctg ctc aag aag tgg     864
Leu Lys Gly Leu Ala Asn Val Gln Cys Ser Asp Leu Leu Lys Lys Trp
        275                 280                 285 ctg ccg caa cgc tgt gcg acc ttt gcc agc aag atc cag ggc cag gtg     912
Leu Pro Gln Arg Cys Ala Thr Phe Ala Ser Lys Ile Gln Gly Gln Val
290                 295                 300 gac aag atc aag ggg gcc ggt ggt gac taa                             942
Asp Lys Ile Lys Gly Ala Gly Gly Asp
305                 310

<210> SEQ ID NO 13
<211> LENGTH: 181
<212> TYPE: PRT
<213> ORGANISM: Artificial
<220> FEATURE:
<223> OTHER INFORMATION: Synthetic Construct

<400> SEQUENCE: 13

Met Asn His Lys Val His His His His His Met Phe Thr Leu Ala
1               5                   10                  15

Asp Phe Val Gly Asp Trp Gln Gln Thr Ala Gly Tyr Asn Gln Asp Gln
            20                  25                  30

Val Leu Glu Gln Gly Gly Leu Ser Ser Leu Phe Gln Ala Leu Gly Val
        35                  40                  45

Ser Val Thr Pro Ile Gln Lys Val Val Leu Ser Gly Glu Asn Gly Leu
    50                  55                  60

Lys Ala Asp Ile His Val Ile Ile Pro Tyr Glu Gly Leu Ser Gly Phe
65                  70                  75                  80

Gln Met Gly Leu Ile Glu Met Ile Phe Lys Val Val Tyr Pro Val Asp
                85                  90                  95

Asp His His Phe Lys Ile Ile Leu His Tyr Gly Thr Leu Val Ile Asp
            100                 105                 110

Gly Val Thr Pro Asn Met Ile Asp Tyr Phe Gly Arg Pro Tyr Pro Gly
        115                 120                 125

Ile Ala Val Phe Asp Gly Lys Gln Ile Thr Val Thr Gly Thr Leu Trp
    130                 135                 140

Asn Gly Asn Lys Ile Tyr Asp Glu Arg Leu Ile Asn Pro Asp Gly Ser
145                 150                 155                 160

Leu Leu Phe Arg Val Thr Ile Asn Gly Val Thr Gly Trp Arg Leu Cys
                165                 170                 175

Glu Asn Ile Leu Ala
            180

<210> SEQ ID NO 14
<211> LENGTH: 546
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(546)

<400> SEQUENCE: 14 atg aat cac aaa gtg cat cat cat cat cat cat atg ttt acg ttg gca    48
Met Asn His Lys Val His His His His His His Met Phe Thr Leu Ala
1               5                   10                  15 gat ttc gtt gga gac tgg caa cag aca gct gga tac aac caa gat caa    96
Asp Phe Val Gly Asp Trp Gln Gln Thr Ala Gly Tyr Asn Gln Asp Gln
```

```
                Asp Phe Val Gly Asp Trp Gln Gln Thr Ala Gly Tyr Asn Gln Asp Gln
                                20                  25                  30 gtg tta gaa caa gga gga ttg tct agt ctg ttc caa gcc ctg gga gtg        144
Val Leu Glu Gln Gly Gly Leu Ser Ser Leu Phe Gln Ala Leu Gly Val
         35                  40                  45 tca gtc acg ccc ata cag aaa gtt gta ctg tct ggg gag aat ggg tta        192
Ser Val Thr Pro Ile Gln Lys Val Val Leu Ser Gly Glu Asn Gly Leu
 50                  55                  60 aaa gct gat att cat gtc ata ata cct tac gag gga ctc agt ggt ttt        240
Lys Ala Asp Ile His Val Ile Ile Pro Tyr Glu Gly Leu Ser Gly Phe
 65                  70                  75                  80 caa atg ggt cta att gaa atg atc ttc aaa gtt gtt tac ccc gtg gat        288
Gln Met Gly Leu Ile Glu Met Ile Phe Lys Val Val Tyr Pro Val Asp
                 85                  90                  95 gat cat cat ttc aag att att ctc cat tat ggt aca ctc gtt att gac        336
Asp His His Phe Lys Ile Ile Leu His Tyr Gly Thr Leu Val Ile Asp
                100                 105                 110 ggt gta aca ccc aac atg att gac tac ttt gga aga cct tac cct gga        384
Gly Val Thr Pro Asn Met Ile Asp Tyr Phe Gly Arg Pro Tyr Pro Gly
            115                 120                 125 att gct gta ttt gac ggc aag cag atc aca gtt act gga act ctg tgg        432
Ile Ala Val Phe Asp Gly Lys Gln Ile Thr Val Thr Gly Thr Leu Trp
130                 135                 140 aac ggc aac aag atc tat gat gag agg cta atc aac cct gat ggt tca        480
Asn Gly Asn Lys Ile Tyr Asp Glu Arg Leu Ile Asn Pro Asp Gly Ser
145                 150                 155                 160 ctc ctc ttc aga gtt act atc aat gga gtc acg gga tgg agg ctt tgc        528
Leu Leu Phe Arg Val Thr Ile Asn Gly Val Thr Gly Trp Arg Leu Cys
                165                 170                 175 gag aac att ctt gcc taa                                                546
Glu Asn Ile Leu Ala
            180

<210> SEQ ID NO 15
<211> LENGTH: 314
<212> TYPE: PRT
<213> ORGANISM: Artificial
<220> FEATURE:
<223> OTHER INFORMATION: Synthetic Construct

<400> SEQUENCE: 15

Met Asn His Lys Val His His His His His Met Ala Gln His Asp
 1               5                  10                  15

Glu Ala Val Asp Asn Lys Phe Asn Lys Glu Gln Gln Asn Ala Phe Tyr
                20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
 50                  55                  60

Glu Ala Lys Lys Leu Asn Asp Ala Gln Ala Pro Lys Val Asp Asn Lys
 65                  70                  75                  80

Phe Asn Lys Glu Gln Gln Asn Ala Phe Tyr Glu Ile Leu His Leu Pro
                 85                  90                  95

Asn Leu Asn Glu Glu Gln Arg Asn Ala Phe Ile Gln Ser Leu Lys Asp
                100                 105                 110

Asp Pro Ser Gln Ser Ala Asn Leu Leu Ala Glu Ala Lys Lys Leu Asn
            115                 120                 125

Asp Ala Gln Ala Pro Lys Val Asp Ala Asn Ser Ser Ser Gly Ser Glu
130                 135                 140
```

-continued

```
Phe Phe Thr Leu Ala Asp Phe Val Gly Asp Trp Gln Gln Thr Ala Gly
145                 150                 155                 160

Tyr Asn Gln Asp Gln Val Leu Glu Gln Gly Leu Ser Ser Leu Phe
            165                 170                 175

Gln Ala Leu Gly Val Ser Val Thr Pro Ile Gln Lys Val Leu Ser
            180                 185                 190

Gly Glu Asn Gly Leu Lys Ala Asp Ile His Val Ile Pro Tyr Glu
            195                 200                 205

Gly Leu Ser Gly Phe Gln Met Gly Leu Ile Glu Met Ile Phe Lys Val
210                 215                 220

Val Tyr Pro Val Asp Asp His His Phe Lys Ile Ile Leu His Tyr Gly
225                 230                 235                 240

Thr Leu Val Ile Asp Gly Val Thr Pro Asn Met Ile Asp Tyr Phe Gly
                    245                 250                 255

Arg Pro Tyr Pro Gly Ile Ala Val Phe Asp Gly Lys Gln Ile Thr Val
                260                 265                 270

Thr Gly Thr Leu Trp Asn Gly Asn Lys Ile Tyr Asp Glu Arg Leu Ile
                    275                 280                 285

Asn Pro Asp Gly Ser Leu Leu Phe Arg Val Thr Ile Asn Gly Val Thr
290                 295                 300

Gly Trp Arg Leu Cys Glu Asn Ile Leu Ala
305                 310
```

<210> SEQ ID NO 16
<211> LENGTH: 945
<212> TYPE: DNA
<213> ORGANISM: Artificial
<220> FEATURE:
<223> OTHER INFORMATION: Synthetic Construct Designed for recombinant
    protein production
<220> FEATURE:
<221> NAME/KEY: CDS
<222> LOCATION: (1)..(945)

<400> SEQUENCE: 16

```
atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
                20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
            35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
        50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat     384
Asp Pro Ser Gln Ser Ala Asn Leu Leu Ala Glu Ala Lys Lys Leu Asn
        115                 120                 125
```

```
gat gct cag gcg ccg aaa gta gac gca aat tcg agc tcg gga tcc gaa      432
Asp Ala Gln Ala Pro Lys Val Asp Ala Asn Ser Ser Ser Gly Ser Glu
        130                 135                 140 ttc ttt acg ttg gca gat ttc gtt gga gac tgg caa cag aca gct gga      480
Phe Phe Thr Leu Ala Asp Phe Val Gly Asp Trp Gln Gln Thr Ala Gly
145                 150                 155                 160 tac aac caa gat caa gtg tta gaa caa gga gga ttg tct agt ctg ttc      528
Tyr Asn Gln Asp Gln Val Leu Glu Gln Gly Gly Leu Ser Ser Leu Phe
                165                 170                 175 caa gcc ctg gga gtg tca gtc acg ccc ata cag aaa gtt gta ctg tct      576
Gln Ala Leu Gly Val Ser Val Thr Pro Ile Gln Lys Val Val Leu Ser
            180                 185                 190 ggg gag aat ggg tta aaa gct gat att cat gtc ata ata cct tac gag      624
Gly Glu Asn Gly Leu Lys Ala Asp Ile His Val Ile Ile Pro Tyr Glu
        195                 200                 205 gga ctc agt ggt ttt caa atg ggt cta att gaa atg atc ttc aaa gtt      672
Gly Leu Ser Gly Phe Gln Met Gly Leu Ile Glu Met Ile Phe Lys Val
    210                 215                 220 gtt tac ccc gtg gat gat cat cat ttc aag att att ctc cat tat ggt      720
Val Tyr Pro Val Asp Asp His His Phe Lys Ile Ile Leu His Tyr Gly
225                 230                 235                 240 aca ctc gtt att gac ggt gta aca ccc aac atg att gac tac ttt gga      768
Thr Leu Val Ile Asp Gly Val Thr Pro Asn Met Ile Asp Tyr Phe Gly
                245                 250                 255 aga cct tac cct gga att gct gta ttt gac ggc aag cag atc aca gtt      816
Arg Pro Tyr Pro Gly Ile Ala Val Phe Asp Gly Lys Gln Ile Thr Val
            260                 265                 270 act gga act ctg tgg aac ggc aac aag atc tat gat gag agg cta atc      864
Thr Gly Thr Leu Trp Asn Gly Asn Lys Ile Tyr Asp Glu Arg Leu Ile
        275                 280                 285 aac cct gat ggt tca ctc ctc ttc aga gtt act atc aat gga gtc acg      912
Asn Pro Asp Gly Ser Leu Leu Phe Arg Val Thr Ile Asn Gly Val Thr
    290                 295                 300 gga tgg agg ctt tgc gag aac att ctt gcc taa                          945
Gly Trp Arg Leu Cys Glu Asn Ile Leu Ala
305                 310

<210> SEQ ID NO 17
<211> LENGTH: 319
<212> TYPE: PRT
<213> ORGANISM: Artificial
<220> FEATURE:
<223> OTHER INFORMATION: Synthetic Construct

<400> SEQUENCE: 17

Met Asn His Lys Val His His His His His Met Ala Gln His Asp
1               5                   10                  15

Glu Ala Val Asp Asn Lys Phe Asn Lys Glu Gln Gln Asn Ala Phe Tyr
                20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
        50                  55                  60

Glu Ala Lys Lys Leu Asn Asp Ala Gln Ala Pro Lys Val Asp Asn Lys
65                  70                  75                  80

Phe Asn Lys Glu Gln Gln Asn Ala Phe Tyr Glu Ile Leu His Leu Pro
                85                  90                  95

Asn Leu Asn Glu Glu Gln Arg Asn Ala Phe Ile Gln Ser Leu Lys Asp
            100                 105                 110
```

```
Asp Pro Ser Gln Ser Ala Asn Leu Leu Ala Glu Ala Lys Lys Leu Asn
            115                 120                 125

Asp Ala Gln Ala Pro Lys Val Asp Ala Asn Ser Ser Gly Ser Leu
        130                 135                 140

Val Pro Arg Glu Ser Glu Phe Lys Pro Thr Glu Asn Asn Glu Asp Phe
145                 150                 155                 160

Asn Ile Val Ala Val Ala Ser Asn Phe Ala Thr Thr Asp Leu Asp Ala
                165                 170                 175

Asp Arg Gly Lys Leu Pro Gly Lys Lys Leu Pro Leu Glu Val Leu Lys
                180                 185                 190

Glu Met Glu Ala Asn Ala Arg Lys Ala Gly Cys Thr Arg Gly Cys Leu
            195                 200                 205

Ile Cys Leu Ser His Ile Lys Cys Thr Pro Lys Met Lys Lys Phe Ile
        210                 215                 220

Pro Gly Arg Cys His Thr Tyr Glu Gly Asp Lys Glu Ser Ala Gln Gly
225                 230                 235                 240

Gly Ile Gly Glu Ala Ile Val Asp Ile Pro Glu Ile Pro Gly Phe Lys
                245                 250                 255

Asp Leu Glu Pro Met Glu Gln Phe Ile Ala Gln Val Asp Leu Cys Val
                260                 265                 270

Asp Cys Thr Thr Gly Cys Leu Lys Gly Leu Ala Asn Val Gln Cys Ser
            275                 280                 285

Asp Leu Leu Lys Lys Trp Leu Pro Gln Arg Cys Ala Thr Phe Ala Ser
        290                 295                 300

Lys Ile Gln Gly Gln Val Asp Lys Ile Lys Gly Ala Gly Gly Asp
305                 310                 315

<210> SEQ ID NO 18
<211> LENGTH: 960
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(960)

<400> SEQUENCE: 18 atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
            20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
        35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
    50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
```

```
                Asn Leu Asn Glu Glu Gln Arg Asn Ala Phe Ile Gln Ser Leu Lys Asp
                            100                 105                 110 gac cca agc caa agc gct aac ctt tta gca gaa gct aaa aag cta aat       384
Asp Pro Ser Gln Ser Ala Asn Leu Leu Ala Glu Ala Lys Lys Leu Asn
            115                 120                 125 gat gct cag gcg ccg aaa gta gac gca aat tcg agc tcg gga tct ctg       432
Asp Ala Gln Ala Pro Lys Val Asp Ala Asn Ser Ser Ser Gly Ser Leu
130                 135                 140 gtt ccg cgt gaa tcc gaa ttc aag ccc acc gag aac aac gaa gac ttc       480
Val Pro Arg Glu Ser Glu Phe Lys Pro Thr Glu Asn Asn Glu Asp Phe
145                 150                 155                 160 aac atc gtg gcc gtg gcc agc aac ttc gcg acc acg gat ctc gat gct       528
Asn Ile Val Ala Val Ala Ser Asn Phe Ala Thr Thr Asp Leu Asp Ala
                165                 170                 175 gac cgc ggg aag ttg ccc ggc aag aag ctg ccg ctg gag gtg ctc aaa       576
Asp Arg Gly Lys Leu Pro Gly Lys Lys Leu Pro Leu Glu Val Leu Lys
            180                 185                 190 gag atg gaa gcc aat gcc cgg aaa gct ggc tgc acc agg ggc tgt ctg       624
Glu Met Glu Ala Asn Ala Arg Lys Ala Gly Cys Thr Arg Gly Cys Leu
        195                 200                 205 atc tgc ctg tcc cac atc aag tgc acg ccc aag atg aag aag ttc atc       672
Ile Cys Leu Ser His Ile Lys Cys Thr Pro Lys Met Lys Lys Phe Ile
210                 215                 220 cca gga cgc tgc cac acc tac gaa ggc gac aaa gag tcc gca cag ggc       720
Pro Gly Arg Cys His Thr Tyr Glu Gly Asp Lys Glu Ser Ala Gln Gly
225                 230                 235                 240 ggc ata ggc gag gcg atc gtc gac att cct gag att cct ggg ttc aag       768
Gly Ile Gly Glu Ala Ile Val Asp Ile Pro Glu Ile Pro Gly Phe Lys
                245                 250                 255 gac ttg gag ccc atg gag cag ttc atc gca cag gtc gat ctg tgt gtg       816
Asp Leu Glu Pro Met Glu Gln Phe Ile Ala Gln Val Asp Leu Cys Val
            260                 265                 270 gac tgc aca act ggc tgc ctc aaa ggg ctt gcc aac gtg cag tgt tct       864
Asp Cys Thr Thr Gly Cys Leu Lys Gly Leu Ala Asn Val Gln Cys Ser
        275                 280                 285 gac ctg ctc aag aag tgg ctg ccg caa cgc tgt gcg acc ttt gcc agc       912
Asp Leu Leu Lys Lys Trp Leu Pro Gln Arg Cys Ala Thr Phe Ala Ser
290                 295                 300 aag atc cag ggc cag gtg gac aag atc aag ggg gcc ggt ggt gac taa       960
Lys Ile Gln Gly Gln Val Asp Lys Ile Lys Gly Ala Gly Gly Asp
305                 310                 315

<210> SEQ ID NO 19
<211> LENGTH: 321
<212> TYPE: PRT
<213> ORGANISM: Artificial
<220> FEATURE:
<223> OTHER INFORMATION: Synthetic Construct

<400> SEQUENCE: 19

Met Asn His Lys Val His His His His His Met Ala Gln His Asp
1               5                   10                  15

Glu Ala Val Asp Asn Lys Phe Asn Lys Glu Gln Gln Asn Ala Phe Tyr
                20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
        50                  55                  60

Glu Ala Lys Lys Leu Asn Asp Ala Gln Ala Pro Lys Val Asp Asn Lys
65                  70                  75                  80
```

```
Phe Asn Lys Glu Gln Gln Asn Ala Phe Tyr Glu Ile Leu His Leu Pro
             85                  90                  95

Asn Leu Asn Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125

Asp Ala Gln Ala Pro Lys Val Asp Ala Asn Ser Ser Gly Ser Leu
130             135                 140

Glu Val Leu Phe Gln Gly Pro Glu Phe Lys Pro Thr Glu Asn Asn Glu
145             150                 155                 160

Asp Phe Asn Ile Val Ala Val Ala Ser Asn Phe Ala Thr Thr Asp Leu
                165                 170                 175

Asp Ala Asp Arg Gly Lys Leu Pro Gly Lys Lys Leu Pro Leu Glu Val
            180                 185                 190

Leu Lys Glu Met Glu Ala Asn Ala Arg Lys Ala Gly Cys Thr Arg Gly
        195                 200                 205

Cys Leu Ile Cys Leu Ser His Ile Lys Cys Thr Pro Lys Met Lys Lys
    210                 215                 220

Phe Ile Pro Gly Arg Cys His Thr Tyr Glu Gly Asp Lys Glu Ser Ala
225                 230                 235                 240

Gln Gly Gly Ile Gly Glu Ala Ile Val Asp Ile Pro Glu Ile Pro Gly
                245                 250                 255

Phe Lys Asp Leu Glu Pro Met Glu Gln Phe Ile Ala Gln Val Asp Leu
            260                 265                 270

Cys Val Asp Cys Thr Thr Gly Cys Leu Lys Gly Leu Ala Asn Val Gln
        275                 280                 285

Cys Ser Asp Leu Leu Lys Lys Trp Leu Pro Gln Arg Cys Ala Thr Phe
    290                 295                 300

Ala Ser Lys Ile Gln Gly Gln Val Asp Lys Ile Lys Gly Ala Gly Gly
305                 310                 315                 320

Asp

<210> SEQ ID NO 20
<211> LENGTH: 966
<212> TYPE: DNA
<213> ORGANISM: Artificial
<220> FEATURE:
<223> OTHER INFORMATION: Synthetic Construct Designed for recombinant
      protein production
<220> FEATURE:
<221> NAME/KEY: CDS
<222> LOCATION: (1)..(966)

<400> SEQUENCE: 20 atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
                20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
            35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
        50                  55                  60 gaa gct aaa aag cta aat gat gct cag gcg ccg aaa gta gac aac aaa     240
```

```
Glu Ala Lys Lys Leu Asn Asp Ala Gln Ala Pro Lys Val Asp Asn Lys
 65                  70                  75                  80 ttc aac aaa gaa caa caa aac gcg ttc tat gag atc tta cat tta cct       288
Phe Asn Lys Glu Gln Gln Asn Ala Phe Tyr Glu Ile Leu His Leu Pro
                 85                  90                  95 aac tta aac gaa gaa caa cga aac gcc ttc atc caa agt tta aaa gat       336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat       384
Asp Pro Ser Gln Ser Ala Asn Leu Leu Ala Glu Ala Lys Lys Leu Asn
        115                 120                 125 gat gct cag gcg ccg aaa gta gac gca aat tcg agc tcg gga tct ctg       432
Asp Ala Gln Ala Pro Lys Val Asp Ala Asn Ser Ser Ser Gly Ser Leu
    130                 135                 140 gaa gtt ctg ttc cag ggg ccc gaa ttc aag ccc acc gag aac aac gaa       480
Glu Val Leu Phe Gln Gly Pro Glu Phe Lys Pro Thr Glu Asn Asn Glu
145                 150                 155                 160 gac ttc aac atc gtg gcc gtg gcc agc aac ttc gcg acc acg gat ctc       528
Asp Phe Asn Ile Val Ala Val Ala Ser Asn Phe Ala Thr Thr Asp Leu
                165                 170                 175 gat gct gac cgc ggg aag ttg ccc ggc aag aag ctg ccg ctg gag gtg       576
Asp Ala Asp Arg Gly Lys Leu Pro Gly Lys Lys Leu Pro Leu Glu Val
            180                 185                 190 ctc aaa gag atg gaa gcc aat gcc cgg aaa gct ggc tgc acc agg ggc       624
Leu Lys Glu Met Glu Ala Asn Ala Arg Lys Ala Gly Cys Thr Arg Gly
        195                 200                 205 tgt ctg atc tgc ctg tcc cac atc aag tgc acg ccc aag atg aag aag       672
Cys Leu Ile Cys Leu Ser His Ile Lys Cys Thr Pro Lys Met Lys Lys
    210                 215                 220 ttc atc cca gga cgc tgc cac acc tac gaa ggc gac aaa gag tcc gca       720
Phe Ile Pro Gly Arg Cys His Thr Tyr Glu Gly Asp Lys Glu Ser Ala
225                 230                 235                 240 cag ggc ggc ata ggc gag gcg atc gtc gac att cct gag att cct ggg       768
Gln Gly Gly Ile Gly Glu Ala Ile Val Asp Ile Pro Glu Ile Pro Gly
                245                 250                 255 ttc aag gac ttg gag ccc atg gag cag ttc atc gca cag gtc gat ctg       816
Phe Lys Asp Leu Glu Pro Met Glu Gln Phe Ile Ala Gln Val Asp Leu
            260                 265                 270 tgt gtg gac tgc aca act ggc tgc ctc aaa ggg ctt gcc aac gtg cag       864
Cys Val Asp Cys Thr Thr Gly Cys Leu Lys Gly Leu Ala Asn Val Gln
        275                 280                 285 tgt tct gac ctg ctc aag aag tgg ctg ccg caa cgc tgt gcg acc ttt       912
Cys Ser Asp Leu Leu Lys Lys Trp Leu Pro Gln Arg Cys Ala Thr Phe
    290                 295                 300 gcc agc aag atc cag ggc cag gtg gac aag atc aag ggg gcc ggt ggt       960
Ala Ser Lys Ile Gln Gly Gln Val Asp Lys Ile Lys Gly Ala Gly Gly
305                 310                 315                 320 gac taa                                                               966
Asp

<210> SEQ ID NO 21
<211> LENGTH: 188
<212> TYPE: PRT
<213> ORGANISM: Aequorea victoria

<400> SEQUENCE: 21

Lys Leu Thr Ser Asp Phe Asp Asn Pro Arg Trp Ile Gly Arg His Lys
1               5                   10                  15

His Met Phe Asn Phe Leu Asp Val Asn His Asn Gly Lys Ile Ser Leu
            20                  25                  30
```

```
Asp Glu Met Val Tyr Lys Ala Ser Asp Ile Val Ile Asn Asn Leu Gly
            35                  40                  45

Ala Thr Pro Glu Gln Ala Lys Arg His Lys Asp Ala Val Glu Ala Phe
        50                  55                  60

Phe Gly Gly Ala Gly Met Lys Tyr Gly Val Glu Thr Asp Trp Pro Ala
65                  70                  75                  80

Tyr Ile Glu Gly Trp Lys Lys Leu Ala Thr Asp Glu Leu Glu Lys Tyr
                85                  90                  95

Ala Lys Asn Glu Pro Thr Leu Ile Arg Ile Trp Gly Asp Ala Leu Phe
            100                 105                 110

Asn Ile Val Asp Lys Asp Gln Asn Gly Ala Ile Thr Leu Asp Glu Trp
        115                 120                 125

Lys Ala Tyr Thr Lys Ala Ala Gly Ile Ile Gln Ser Ser Glu Asp Cys
130                 135                 140

Glu Glu Thr Phe Arg Val Cys Asp Ile Asp Glu Ser Gly Gln Leu Asp
145                 150                 155                 160

Val Asp Glu Met Thr Arg Gln His Leu Gly Phe Trp Tyr Thr Met Asp
                165                 170                 175

Pro Ala Cys Glu Lys Leu Tyr Gly Gly Ala Val Pro
            180                 185
```

<210> SEQ ID NO 22
<211> LENGTH: 564
<212> TYPE: DNA
<213> ORGANISM: Aequorea victoria
<220> FEATURE:
<221> NAME/KEY: CDS
<222> LOCATION: (1)..(564)

<400> SEQUENCE: 22

```
aaa ctt aca tca gac ttc gac aac cca aga tgg att gga cga cac aag      48
Lys Leu Thr Ser Asp Phe Asp Asn Pro Arg Trp Ile Gly Arg His Lys
1               5                   10                  15 cac atg ttc aat ttc ctt gat gtc aac cac aat gga aaa atc tct ctt      96
His Met Phe Asn Phe Leu Asp Val Asn His Asn Gly Lys Ile Ser Leu
            20                  25                  30 gac gag atg gtc tac aag gca tct gat att gtc atc aat aac ctt gga     144
Asp Glu Met Val Tyr Lys Ala Ser Asp Ile Val Ile Asn Asn Leu Gly
        35                  40                  45 gca aca cct gag caa gcc aaa cga cac aaa gat gct gta gaa gcc ttc     192
Ala Thr Pro Glu Gln Ala Lys Arg His Lys Asp Ala Val Glu Ala Phe
    50                  55                  60 ttc gga gga gct gga atg aaa tat ggt gtg gaa act gat tgg cct gca     240
Phe Gly Gly Ala Gly Met Lys Tyr Gly Val Glu Thr Asp Trp Pro Ala
65                  70                  75                  80 tat att gaa gga tgg aaa aaa ttg gct act gat gaa ttg gag aaa tac     288
Tyr Ile Glu Gly Trp Lys Lys Leu Ala Thr Asp Glu Leu Glu Lys Tyr
            85                  90                  95 gcc aaa aac gaa cca acg ctc atc cgt ata tgg ggt gat gct ttg ttt     336
Ala Lys Asn Glu Pro Thr Leu Ile Arg Ile Trp Gly Asp Ala Leu Phe
            100                 105                 110 aat atc gtt gac aaa gat caa aat gga gcc att aca ctg gat gaa tgg     384
Asn Ile Val Asp Lys Asp Gln Asn Gly Ala Ile Thr Leu Asp Glu Trp
        115                 120                 125 aaa gca tac acc aaa gct gct ggt atc atc caa tca tca gaa gat tgc     432
Lys Ala Tyr Thr Lys Ala Ala Gly Ile Ile Gln Ser Ser Glu Asp Cys
130                 135                 140 gag gaa aca ttc aga gtg tgc gat att gat gaa agt gga caa ctc gat     480
Glu Glu Thr Phe Arg Val Cys Asp Ile Asp Glu Ser Gly Gln Leu Asp
145                 150                 155                 160
```

```
Glu Glu Thr Phe Arg Val Cys Asp Ile Asp Glu Ser Gly Gln Leu Asp
145                 150                 155                 160 gtt gat gag atg aca aga caa cat tta gga ttt tgg tac act atg gac   528
Val Asp Glu Met Thr Arg Gln His Leu Gly Phe Trp Tyr Thr Met Asp
                165                 170                 175 cct gct tgc gaa aag ctc tac ggt gga gct gtc ccc                   564
Pro Ala Cys Glu Lys Leu Tyr Gly Gly Ala Val Pro
            180                 185

<210> SEQ ID NO 23
<211> LENGTH: 168
<212> TYPE: PRT
<213> ORGANISM: Gaussia princeps

<400> SEQUENCE: 23

Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
            20                  25                  30

Lys Lys Leu Pro Leu Glu Val Leu Lys Glu Met Glu Ala Asn Ala Arg
        35                  40                  45

Lys Ala Gly Cys Thr Arg Gly Cys Leu Ile Cys Leu Ser His Ile Lys
    50                  55                  60

Cys Thr Pro Lys Met Lys Lys Phe Ile Pro Gly Arg Cys His Thr Tyr
65                  70                  75                  80

Glu Gly Asp Lys Glu Ser Ala Gln Gly Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165

<210> SEQ ID NO 24
<211> LENGTH: 504
<212> TYPE: DNA
<213> ORGANISM: Gaussia princeps
<220> FEATURE:
<221> NAME/KEY: CDS
<222> LOCATION: (1)..(504)

<400> SEQUENCE: 24 aag ccc acc gag aac aac gaa gac ttc aac atc gtg gcc gtg gcc agc    48
Lys Pro Thr Glu Asn Asn Glu Asp Phe Asn Ile Val Ala Val Ala Ser
1               5                   10                  15 aac ttc gcg acc acg gat ctc gat gct gac cgc ggg aag ttg ccc ggc    96
Asn Phe Ala Thr Thr Asp Leu Asp Ala Asp Arg Gly Lys Leu Pro Gly
            20                  25                  30 aag aag ctg ccg ctg gag gtg ctc aaa gag atg gaa gcc aat gcc cgg   144
Lys Lys Leu Pro Leu Glu Val Leu Lys Glu Met Glu Ala Asn Ala Arg
        35                  40                  45 aaa gct ggc tgc acc agg ggc tgt ctg atc tgc ctg tcc cac atc aag   192
Lys Ala Gly Cys Thr Arg Gly Cys Leu Ile Cys Leu Ser His Ile Lys
    50                  55                  60
```

```
tgc acg ccc aag atg aag aag ttc atc cca gga cgc tgc cac acc tac    240
Cys Thr Pro Lys Met Lys Lys Phe Ile Pro Gly Arg Cys His Thr Tyr
 65                  70                  75                  80 gaa ggc gac aaa gag tcc gca cag ggc gga ata ggc gag gcg atc gtc    288
Glu Gly Asp Lys Glu Ser Ala Gln Gly Gly Ile Gly Glu Ala Ile Val
                 85                  90                  95 gac att cct gag att cct ggg ttc aag gac ttg gag ccc atg gag cag    336
Asp Ile Pro Glu Ile Pro Gly Phe Lys Asp Leu Glu Pro Met Glu Gln
            100                 105                 110 ttc atc gca cag gtc gat ctg tgt gtg gac tgc aca act ggc tgc ctc    384
Phe Ile Ala Gln Val Asp Leu Cys Val Asp Cys Thr Thr Gly Cys Leu
        115                 120                 125 aaa ggg ctt gcc aac gtg cag tgt tct gac ctg ctc aag aag tgg ctg    432
Lys Gly Leu Ala Asn Val Gln Cys Ser Asp Leu Leu Lys Lys Trp Leu
    130                 135                 140 ccg caa cgc tgt gcg acc ttt gcc agc aag atc cag ggc cag gtg gac    480
Pro Gln Arg Cys Ala Thr Phe Ala Ser Lys Ile Gln Gly Gln Val Asp
145                 150                 155                 160 aag atc aag ggg gcc ggt ggt gac                                    504
Lys Ile Lys Gly Ala Gly Gly Asp
                165

<210> SEQ ID NO 25
<211> LENGTH: 169
<212> TYPE: PRT
<213> ORGANISM: Oplophorus gracilorostris

<400> SEQUENCE: 25

Phe Thr Leu Ala Asp Phe Val Gly Asp Trp Gln Gln Thr Ala Gly Tyr
 1               5                  10                  15

Asn Gln Asp Gln Val Leu Glu Gln Gly Gly Leu Ser Ser Leu Phe Gln
             20                  25                  30

Ala Leu Gly Val Ser Val Thr Pro Ile Gln Lys Val Val Leu Ser Gly
         35                  40                  45

Glu Asn Gly Leu Lys Ala Asp Ile His Val Ile Pro Tyr Glu Gly Leu
     50                  55                  60

Leu Ser Gly Phe Gln Met Gly Leu Ile Glu Met Ile Phe Lys Val Val
 65                  70                  75                  80

Tyr Pro Val Asp Asp His His Phe Lys Ile Ile Leu His Tyr Gly Thr
                 85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 26
<211> LENGTH: 507
<212> TYPE: DNA
<213> ORGANISM: Oplophorus gracilorostris
<220> FEATURE:
<221> NAME/KEY: CDS
<222> LOCATION: (1)..(507)

<400> SEQUENCE: 26
```

-continued

```
ttt acg ttg gca gat ttc gtt gga gac tgg caa cag aca gct gga tac     48
Phe Thr Leu Ala Asp Phe Val Gly Asp Trp Gln Gln Thr Ala Gly Tyr
 1               5                  10                  15 aac caa gat caa gtg tta gaa caa gga gga ttg tct agt ctg ttc caa     96
Asn Gln Asp Gln Val Leu Glu Gln Gly Gly Leu Ser Ser Leu Phe Gln
             20                  25                  30 gcc ctg gga gtg tca gtc acg ccc ata cag aaa gtt gta ctg tct ggg    144
Ala Leu Gly Val Ser Val Thr Pro Ile Gln Lys Val Val Leu Ser Gly
         35                  40                  45 gag aat ggg tta aaa gct gat att cat gtc ata ata cct tac gag gga    192
Glu Asn Gly Leu Lys Ala Asp Ile His Val Ile Ile Pro Tyr Glu Gly
     50                  55                  60 ctc agt ggt ttt caa atg ggt cta att gaa atg atc ttc aaa gtt gtt    240
Leu Ser Gly Phe Gln Met Gly Leu Ile Glu Met Ile Phe Lys Val Val
 65                  70                  75                  80 tac ccc gtg gat gat cat cat ttc aag att att ctc cat tat ggt aca    288
Tyr Pro Val Asp Asp His His Phe Lys Ile Ile Leu His Tyr Gly Thr
                 85                  90                  95 ctc gtt att gac ggt gta aca ccc aac atg att gac tac ttt gga aga    336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act    384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac    432
Gly Thr Leu Trp Asn Gly Asn Lys Ile Tyr Asp Glu Arg Leu Ile Asn
130                 135                 140 cct gat ggt tca ctc ctc ttc aga gtt act atc aat gga gtc acg gga    480
Pro Asp Gly Ser Leu Leu Phe Arg Val Thr Ile Asn Gly Val Thr Gly
145                 150                 155                 160 tgg agg ctt tgc gag aac att ctt gcc                                507
Trp Arg Leu Cys Glu Asn Ile Leu Ala
                165
```

<210> SEQ ID NO 27
<211> LENGTH: 36
<212> TYPE: DNA
<213> ORGANISM: Artificial
<220> FEATURE:
<223> OTHER INFORMATION: Primer

<400> SEQUENCE: 27
ccggaattca tgaaacttac atcagacttc gacaac                             36

<210> SEQ ID NO 28
<211> LENGTH: 36
<212> TYPE: DNA
<213> ORGANISM: Artificial
<220> FEATURE:
<223> OTHER INFORMATION: Primer

<400> SEQUENCE: 28
cgcgtcgact tagggacag ctccaccgta gagctt                              36

<210> SEQ ID NO 29
<211> LENGTH: 30
<212> TYPE: DNA
<213> ORGANISM: Artificial
<220> FEATURE:
<223> OTHER INFORMATION: Primer

<400> SEQUENCE: 29
ccgcatatgg cgcaacacga tgaagccgtg                                    30

<210> SEQ ID NO 30
<211> LENGTH: 30
<212> TYPE: DNA
<213> ORGANISM: Artificial
<220> FEATURE:
<223> OTHER INFORMATION: Primer

<400> SEQUENCE: 30
ggcggatccc gagctcgaat ttgcgtctac                                    30

<210> SEQ ID NO 31
<211> LENGTH: 30
<212> TYPE: DNA
<213> ORGANISM: Artificial
<220> FEATURE:
<223> OTHER INFORMATION: Primer

<400> SEQUENCE: 31
gccgagctca gcccaccga gaacaacgaa                                     30

<210> SEQ ID NO 32
<211> LENGTH: 30
<212> TYPE: DNA
<213> ORGANISM: Artificial
<220> FEATURE:
<223> OTHER INFORMATION: Primer

<400> SEQUENCE: 32
gccgaattct tagtcaccac cggccccctt                                    30

<210> SEQ ID NO 33
<211> LENGTH: 30
<212> TYPE: DNA
<213> ORGANISM: Artificial
<220> FEATURE:
<223> OTHER INFORMATION: Primer

<400> SEQUENCE: 33
gccgaattca gcccaccga gaacaacgaa                                     30

<210> SEQ ID NO 34
<211> LENGTH: 30
<212> TYPE: DNA
<213> ORGANISM: Artificial
<220> FEATURE:
<223> OTHER INFORMATION: Primer

<400> SEQUENCE: 34
gcctctagat tagtcaccac cggccccctt                                    30

<210> SEQ ID NO 35
<211> LENGTH: 30
<212> TYPE: DNA
<213> ORGANISM: Artificial
<220> FEATURE:
<223> OTHER INFORMATION: Primer

<400> SEQUENCE: 35
gcgcatatgt ttacgttggc agatttcgtt                                    30

```
<210> SEQ ID NO 36
<211> LENGTH: 36
<212> TYPE: DNA
<213> ORGANISM: Artificial
<220> FEATURE:
<223> OTHER INFORMATION: Primer

<400> SEQUENCE: 36
cgcgaattct taggcaagaa tgttctcgca aagcct                                  36

<210> SEQ ID NO 37
<211> LENGTH: 33
<212> TYPE: DNA
<213> ORGANISM: Artificial
<220> FEATURE:
<223> OTHER INFORMATION: Primer

<400> SEQUENCE: 37
gcggaattct ttacgttggc agatttcgtt gga                                     33

<210> SEQ ID NO 38
<211> LENGTH: 38
<212> TYPE: DNA
<213> ORGANISM: Artificial
<220> FEATURE:
<223> OTHER INFORMATION: Primer

<400> SEQUENCE: 38
ccgctctaga attaggcaag aatgttctcg caaagcct                                38

<210> SEQ ID NO 39
<211> LENGTH: 24
<212> TYPE: DNA
<213> ORGANISM: Artificial
<220> FEATURE:
<223> OTHER INFORMATION: Synthetic Construct Designed for recombinant
      protein production

<400> SEQUENCE: 39
gatctctggt tccgcgtgga tccg                                               24

<210> SEQ ID NO 40
<211> LENGTH: 24
<212> TYPE: DNA
<213> ORGANISM: Artificial
<220> FEATURE:
<223> OTHER INFORMATION: Synthetic Construct Designed for recombinant
      protein production

<400> SEQUENCE: 40
aattcggatc cacgcggaac caga                                               24

<210> SEQ ID NO 41
<211> LENGTH: 30
<212> TYPE: DNA
<213> ORGANISM: Artificial
<220> FEATURE:
<223> OTHER INFORMATION: Synthetic Construct Designed for recombinant
      protein production

<400> SEQUENCE: 41
gatctctgga agttctgttc caggggcccg                                         30

<210> SEQ ID NO 42
<211> LENGTH: 30
<212> TYPE: DNA
<213> ORGANISM: Artificial
```

-continued

```
<220> FEATURE:
<223> OTHER INFORMATION: Synthetic Construct Designed for recombinant
      protein production

<400> SEQUENCE: 42
aattcgggcc cctggaacag aacttccaga                                       30
```

PROCESS FOR PRODUCTION OF RECOMBINANT PROTEINS AS A SOLUBLE FORM

CROSS REFERENCE TO RELATED APPLICATIONS

This application claims priority under 35 U.S.C. §119 to Japanese Patent Application No. JP 2006-253045, filed Sep. 19, 2006, which application is expressly incorporated herein by reference in its entirety.

BACKGROUND OF THE INVENTION

1. Field of the Invention

The invention relates to a method of producing a target protein as soluble protein.

2. Related Art

A large number of recombinant protein expression systems have been developed to date, including, for example, cell-free translation systems and recombinant protein expression systems within hosts such as bacteria, yeast, insects, transgenic animals, and transgenic plants. *Escherichia coli* is widely used as an expression system for heterologous protein because it is easily grown to high densities and because of the progress in research on host vector systems.

However, when a target protein is expressed using these recombinant protein expression systems, incorrect folding by the expressed protein can prevent expression of the functionality of the original protein and can result in the not insignificant formation of insoluble aggregates, known as inclusion bodies. Even when, for example, refolding is carried out in such cases after solubilization of the inclusion body with a denaturant or surfactant, the correctly folded protein exhibiting its native functionality is not necessarily obtained. In addition, even when protein expressing its original functionality is obtained, in many instances a satisfactory recovery rate is not obtained.

Against this background, a method of suppressing the formation of inclusion bodies of an expressed recombinant target protein has not been established to date. As a stand in for such a method, expression as a soluble protein is attempted by fusing the insoluble target protein with the soluble high molecular weight (40,000) maltose-binding protein or glutathione S-transferase (GST) (Fox, J. D. and Waugh, D. S., "Maltose-binding protein as a solubility enhancer." METHODS MOL. BIOL., 205: 99-117 (2003); Ausubel, F. M. et al., editors, CURRENT PROTOCOLS IN MOLECULAR BIOLOGY, Vol. 2, 16.0.1 (1996)). However, there have been problems such as, for example, the soluble protein may not exhibit its original activity or functionality and the target protein may become insoluble when the maltose-binding protein or GST is removed.

The ZZ domain is a synthetic IgG binding region developed on the basis of the IgG binding region of protein A (refer, for example, to Nilsson B. et al., *Protein Eng.*, 1: 107-113 (1987)).

However, in those cases where the ZZ domain of the IgG binding region has been expressed fused with a target protein, there have been no reports of an effect whereby the solubility of the fusion protein is increased, nor have there been reports of an activity that contributes to an efficient refolding of the target protein to the active form of the protein. Up to the present time, the use of the ZZ domain originating from protein A has not gone beyond use, after expression of the fusion protein with a target protein, as a ligand in IgG antibody affinity chromatography in target protein purification. In addition, IgG antibody columns are expensive and there are only limited instances where they can be used even when a genetic recombinant fusion protein utilizing the ZZ domain is employed in mass production.

SUMMARY OF THE INVENTION

In view of these circumstances, the production of a target protein as a soluble protein using a recombinant protein expression system is strongly desired from an industrial standpoint in order to produce a useful protein. In addition, there is also strong desire in research fields such as research into protein structure and function.

It has been observed that a target protein is prepared as a soluble protein when the target protein expression is carried out using an expression vector that includes (1) an expression-inducible promoter sequence;

(2) a first coding sequence including a polynucleotide that encodes the ZZ domain; and (3) a second coding sequence that includes a polynucleotide that encodes a target protein.

The invention was achieved as a result of additional investigations carried out based on this knowledge.

The invention includes:

[1] An expression vector including:

(1) an expression-inducible promoter sequence;

(2) a first coding sequence including polynucleotide coding for polypeptide that is represented by the formula $(Z)_n$ wherein n represents an integer from 1 to 5 and Z represents polypeptide selected from the group of:

(a) a polypeptide including the amino acid sequence of SEQ ID NO: 1, (b) a polypeptide including an amino acid sequence with, in the amino acid sequence of SEQ ID NO: 1, one or more deleted, substituted, inserted and/or added amino acids, (c) a polypeptide including an amino acid sequence that has at least approximately 90% identity with the amino acid sequence of SEQ ID NO: 1, and (d) a polypeptide including an amino acid sequence that is encoded by a polynucleotide that hybridizes under stringent conditions with a polynucleotide including a base sequence that is complementary to the base sequence of SEQ ID NO: 2, and that has the capacity when expressed as a fusion protein with a target protein to render said fusion protein expressible as a soluble protein; and (3) a second coding sequence that includes a polynucleotide that codes for a target protein.

[2] The vector according to item [1], wherein the polypeptide represented by formula $(Z)_n$ is a polypeptide represented by $(Z)_2$.

[3] the vector according to item [2], wherein the polypeptide represented by $(Z)_2$ is a polypeptide selected from the group of (e) a polypeptide including the amino acid sequence of SEQ ID NO: 3, (f) a polypeptide that includes an amino acid sequence with, in the amino acid sequence of SEQ ID NO: 3, one or more deleted, substituted, inserted and/or added amino acids, and that has the capacity when expressed as a fusion protein with a target protein to render said fusion protein expressible as a soluble protein, (g) a polypeptide that includes an amino acid sequence having at least approximately 90% identity with the amino acid sequence of SEQ ID NO: 3, and that has the capacity when expressed as a fusion protein with a target protein to render said fusion protein expressible as a soluble protein, and (h) a polypeptide including an amino acid sequence that is encoded by a polynucleotide that hybridizes under stringent conditions with a polynucleotide including a base sequence that is complementary to the base sequence of SEQ ID NO: 4, and having the capacity when expressed as a fusion protein with a target protein to render said fusion protein expressible as a soluble protein.

[4] The vector according to any of items [1] to [3], wherein the expression-inducible promoter sequence is a low-temperature expression-inducible promoter sequence.

[5] The vector according to item [4], wherein the low-temperature expression-inducible promoter sequence is a promoter sequence for a cold shock gene.

[6] The vector according to item [5], wherein the promoter sequence for a cold shock gene is a promoter sequence for an *Escherichia coli* cold shock gene.

[7] The vector according to item [6], wherein the promoter sequence for an *Escherichia coli* cold shock gene is a promoter sequence for the *Escherichia coli* cold shock gene cspA, cspB, cspG, cspI, or csdA.

[8] The vector according to any of items [1] to [7], further including, between the first coding sequence and the second coding sequence, a coding sequence including a polynucleotide coding for a cleavable linker peptide.

[9] The vector according to item [8], wherein the cleavable linker peptide is a linker peptide having a protease cleavage site.

[10] The vector according to any of items [1] to [9], further including, on the 5' side of the first coding sequence, a coding sequence that includes a polynucleotide that encodes an amino acid sequence that facilitates purification.

[11] The vector according to item [10], wherein the amino acid sequence that facilitates the purification is a histidine tag sequence.

[12] An expression vector including:
(1) an expression-inducible promoter sequence;
(2) a first coding sequence including a polynucleotide coding for polypeptide that is represented by the formula $(Z)_n$ wherein n represents an integer from 1 to 5 and Z represents polypeptide selected from the group of:
(a) a polypeptide including the amino acid sequence of SEQ ID NO: 1,
(b) a polypeptide including an amino acid sequence with, in the amino acid sequence of SEQ ID NO: 1, one or more deleted, substituted, inserted and/or added amino acids,
(c) a polypeptide including an amino acid sequence that has at least approximately 90% identity with the amino acid sequence of SEQ ID NO: 1, and
(d) a polypeptide including an amino acid sequence that is encoded by a polynucleotide that hybridizes under stringent conditions with a polynucleotide including a base sequence that is complementary to the base sequence of SEQ ID NO: 2, and that has the capacity when expressed as a fusion protein with a target protein to render said fusion protein expressible as a soluble protein; and
(3) at least one restriction enzyme site that enables the insertion of a second coding sequence that includes a polynucleotide that codes for a target protein.

[13] The vector according to item [12], wherein the polypeptide represented by formula $(Z)_n$ is a polypeptide represented by $(Z)_2$.

[14] The vector according to item [13], wherein the polypeptide represented by $(Z)_2$ is a polypeptide selected from the group of
(e) a polypeptide including the amino acid sequence of SEQ ID NO: 3, (f) a polypeptide that includes an amino acid sequence with, in the amino acid sequence of SEQ ID NO: 3, one or more deleted, substituted, inserted and/or added amino acids, and that has the capacity when expressed as a fusion protein with a target protein to render said fusion protein expressible as a soluble protein, (g) a polypeptide that includes an amino acid sequence having at least approximately 90% identity with the amino acid sequence of SEQ ID NO: 3, and that has the capacity when expressed as a fusion protein with a target protein to render said fusion protein expressible as a soluble protein, and (h) a polypeptide including an amino acid sequence that is encoded by a polynucleotide that hybridizes under stringent conditions with a polynucleotide including a base sequence that is complementary to the base sequence of SEQ ID NO: 4, and having the capacity when expressed as a fusion protein with a target protein to render said fusion protein expressible as a soluble protein.

[15] The vector according to any of items [12] to [14], wherein the expression-inducible promoter sequence is a low-temperature expression-inducible promoter sequence.

[16] The vector according to item [15], wherein the low-temperature expression-inducible promoter sequence is a promoter sequence for a cold shock gene.

[17] The vector according to item [16], wherein the promoter sequence for a cold shock gene is a promoter sequence for an *Escherichia coli* cold shock gene.

[18] The vector according to item [17], wherein the promoter sequence for an *Escherichia coli* cold shock gene is a promoter sequence for the *Escherichia coli* cold shock gene cspA, cspB, cspG, cspI, or csdA.

[19] The vector according to any of items [12] to [18], further including, between the first coding sequence and the second coding sequence, a coding sequence including a polynucleotide coding for a cleavable linker peptide.

[20] The vector according to item [19], wherein the cleavable linker peptide is a linker peptide having a protease cleavage site.

[21] The vector according to any of items [12] to [20], further including, on the 5' side of the first coding sequence, a coding sequence that includes a polynucleotide that encodes an amino acid sequence that facilitates purification.

[22] The vector according to item [21], wherein the amino acid sequence that facilitates the purification is a histidine tag sequence.

[23] A fusion protein that can be expressed as a soluble protein, including:
(1) a first amino acid sequence including the amino acid sequence of a polypeptide that is represented by the formula $(Z)_n$
wherein n represents an integer from 1 to 5 and Z represents polypeptide selected from the group of:
(a) a polypeptide including the amino acid sequence of SEQ ID NO: 1,
(b) a polypeptide including an amino acid sequence with, in the amino acid sequence of SEQ ID NO: 1, one or more deleted, substituted, inserted and/or added amino acids,
(c) a polypeptide including an amino acid sequence that has at least approximately 90% identity with the amino acid sequence of SEQ ID NO: 1, and
(d) a polypeptide including an amino acid sequence that is encoded by a polynucleotide that hybridizes under stringent conditions with a polynucleotide including a base sequence that is complementary to the base sequence of SEQ ID NO: 2, and that has the capacity when expressed as a fusion protein with a target protein to render said fusion protein expressible as a soluble protein, and (2) a second amino acid sequence including the amino acid sequence of a target protein.

[24] The fusion protein according to item [23], wherein the polypeptide represented by formula $(Z)_n$ is a polypeptide represented by $(Z)_2$.

[25] The fusion protein according to item [24], wherein the polypeptide represented by $(Z)_2$ is a polypeptide selected from the group of (e) a polypeptide including the amino acid sequence of SEQ ID NO: 3, (f) a polypeptide that includes an amino acid sequence with, in the amino acid sequence of SEQ ID NO: 3, one or more deleted, substituted, inserted and/or added amino acids, and that has the capacity when expressed as a fusion protein with a target protein to render said fusion protein expressible as a soluble protein, (g) a polypeptide that includes an amino acid sequence having at least approximately 90% identity with the amino acid sequence of SEQ ID NO: 3, and that has the capacity when expressed as a fusion protein with a target protein to render said fusion protein expressible as a soluble protein, and (h) a polypeptide including an amino acid sequence that is encoded by a polynucleotide that hybridizes under stringent conditions with a polynucleotide including a base sequence that is complementary to the base sequence of SEQ ID NO: 4, and having the capacity when expressed as a fusion protein with a target protein to render said fusion protein expressible as a soluble protein.

[26] The fusion protein according to any of items [23] to [25], wherein the target protein is any one selected from the group of apoaequorin, *Gaussia* luciferase, and *Oplophorus* (shrimp) luciferase.

[27] The fusion protein according to any of items [23] to [26], further including, between the first amino acid sequence and the second amino acid sequence, an amino acid sequence including the amino acid sequence of a cleavable linker peptide.

[28] The fusion protein according to item [27], wherein the cleavable linker peptide is a linker peptide having a protease cleavage site.

[29] The fusion protein according to any of items [23] to [28], further including, on the amino terminal side of the first amino acid sequence, an amino acid sequence that facilitates purification.

[30] The fusion protein according to item [29], wherein the amino acid sequence that facilitates the purification is a histidine tag sequence.

[31] A fusion protein that can be expressed as a soluble protein and that is represented by the formula $(Z)_n$-L-X, wherein n represents an integer from 1 to 5; L represents a cleavable linker peptide; Z represents polypeptide selected from the group of:

(a) a polypeptide including the amino acid sequence of SEQ ID NO: 1, (b) a polypeptide including an amino acid sequence with, in the amino acid sequence of SEQ ID NO: 1, one or more deleted, substituted, inserted and/or added amino acids, (c) a polypeptide including an amino acid sequence that has at least approximately 90% identity with the amino acid sequence of SEQ ID NO: 1, and (d) a polypeptide including an amino acid sequence that is encoded by a polynucleotide that hybridizes under stringent conditions with a polynucleotide including a base sequence that is complementary to the base sequence of SEQ ID NO: 2; and X represents the amino acid sequence of a target protein).

[32] The fusion protein according to item [31], wherein the target protein is any one selected from the group of apoaequorin, *Gaussia* luciferase, and *Oplophorus* (shrimp) luciferase.

[33] A polynucleotide including a polynucleotide that codes for the fusion protein according to any of items [23] to [32].

[34] The polynucleotide according to item [33], that is DNA.

[35] The method of producing a target protein as a soluble protein, including causing the expression of protein using an expression vector which includes:

(1) an expression-inducible promoter sequence;

(2) a first coding sequence including a polynucleotide coding for polypeptide that is represented by the formula $(Z)_n$, wherein n represents an integer from 1 to 5, and Z represents polypeptide selected from the group of:

(a) a polypeptide including the amino acid sequence of SEQ ID NO: 1, (b) a polypeptide including an amino acid sequence with, in the amino acid sequence of SEQ ID NO: 1, one or more deleted, substituted, inserted and/or added amino acids, (c) a polypeptide including an amino acid sequence that has at least approximately 90% identity with the amino acid sequence of SEQ ID NO: 1, and (d) a polypeptide including an amino acid sequence that is encoded by a polynucleotide that hybridizes under stringent conditions with a polynucleotide including a base sequence that is complementary to the base sequence of SEQ ID NO: 2, and that has the capacity when expressed as a fusion protein with a target protein to render said fusion protein expressible as a soluble protein; and (3) a second coding sequence that includes a polynucleotide that codes for a target protein.

[36] The method according to item [35], wherein the polypeptide represented by formula $(Z)_n$ is a polypeptide represented by $(Z)_2$.

[37] The method according to item [36], wherein the polypeptide represented by the formula $(Z)_2$ is a polypeptide selected from the group of (e) a polypeptide including the amino acid sequence of SEQ ID NO: 3, (f) a polypeptide that includes an amino acid sequence with, in the amino acid sequence of SEQ ID NO: 3, one or more deleted, substituted, inserted and/or added amino acids, and that has the capacity when expressed as a fusion protein with a target protein to render said fusion protein expressible as a soluble protein, (g) a polypeptide that includes an amino acid sequence having at least approximately 90% identity with the amino acid sequence of SEQ ID NO: 3, and that has the capacity when expressed as a fusion protein with a target protein to render said fusion protein expressible as a soluble protein, and (h) a polypeptide including an amino acid sequence that is encoded by a polynucleotide that hybridizes under stringent conditions with a polynucleotide including a base sequence that is complementary to the base sequence of SEQ ID NO: 4, and having the capacity when expressed as a fusion protein with a target protein to render said fusion protein expressible as a soluble protein.

[38] The method according to any of items [35] to [37], wherein the expression-inducible promoter sequence is a low-temperature expression-inducible promoter sequence.

[39] The method according to item [38], wherein the low-temperature expression-inducible promoter sequence is a promoter sequence for a cold shock gene.

[40] The method according to item [39], wherein the promoter sequence for a cold shock gene is a promoter sequence for an *Escherichia coli* cold shock gene.

[41] The method according to item [40], wherein the promoter sequence for an *Escherichia coli* cold shock gene is a promoter sequence for the *Escherichia coli* cold shock gene cspA, cspB, cspG, cspI, or csdA.

[42] The method according to any of items [35] to [41], further including, between the first coding sequence and the second coding sequence, a coding sequence including a polynucleotide coding for a cleavable linker peptide.

[43] The method according to item [42], wherein the cleavable linker peptide is a linker peptide having a protease cleavage site.

[44] The method according to any of items [35] to [43], further including, on the 5' side of the first coding sequence, a coding sequence that includes a polynucleotide that encodes an amino acid sequence that facilitates purification.

[45] The method according to item [44], wherein the amino acid sequence that facilitates the purification is a histidine tag sequence.

With regard to the production of a target protein using a recombinant protein expression system, the invention enables the production of the target protein as a soluble protein and thereby eliminates the necessity to denature (solubilize) the target protein. The invention thus makes it possible to efficiently obtain the target protein at a high recovery rate.

The invention is therefore very useful as a method for producing protein, for example, useful protein, protein that is the subject of an analysis of structure and/or function, and so forth.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DESCRIPTION OF THE PREFERRED EMBODIMENTS

Figure 1:
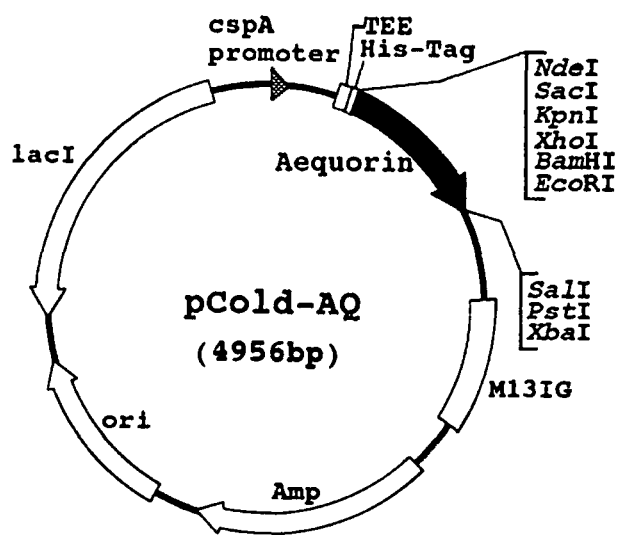
FIG. 1 shows the pCold-AQ expression vector obtained in Reference Example 1.

The invention provides, a fusion protein including
(1) a first amino acid sequence including the amino acid sequence of a polypeptide that is represented by the formula $(Z)_n$ and
(2) a second amino acid sequence including the amino acid sequence of a target protein; a polynucleotide that encodes this fusion protein; and a method of producing the fusion protein using this polynucleotide.

The invention also provides, an expression vector including
(1) an expression-inducible promoter sequence,
(2) a first coding sequence including polynucleotide coding for polypeptide that is represented by the formula $(Z)_n$, and
(3) a second coding sequence that includes polynucleotide that codes for a target protein; and The invention also provides a method of producing this target protein including bringing about the expression of protein using this expression vector. This method of production can produce the target protein in a solubilized state.

The Fusion Protein of the Invention

The fusion protein of the invention includes (1) a first amino acid sequence including the amino acid sequence of a polypeptide that is represented by the formula $(Z)_n$ and (2) a second amino acid sequence including the amino acid sequence of a target protein.

The fusion protein of the invention may also include an amino acid sequence including (3) the amino acid sequence of a cleavable peptide linker.

The fusion protein of the invention is described in greater detail in the following.

The Polypeptide Represented by the Formula $(Z)_n$

The polypeptide represented by the formula $(Z)_n$ has the activity or function when expressed as a fusion protein with a target protein of enabling the fusion protein to be expressed as a soluble protein.

Z represents polypeptide selected from the group of the following (a) to (d):

(a) a polypeptide including the amino acid sequence of SEQ ID NO: 1, (b) a polypeptide including an amino acid sequence with, in the amino acid sequence of SEQ ID NO: 1, one or more deleted, substituted, inserted and/or added amino acids, (c) a polypeptide including an amino acid sequence that has at least approximately 90% identity with the amino acid sequence of SEQ ID NO: 1, and (d) a polypeptide including an amino acid sequence that is encoded by a polynucleotide that hybridizes under stringent conditions with a polynucleotide including a base sequence that is complementary to the base sequence of SEQ ID NO: 2.

In this Specification, the range of "one or more" in "an amino acid sequence having one or more deleted, substituted, inserted and/or added amino acids" is, for example, from 1 to 20, from 1 to 15, from 1 to 10, from 1 to 9, from 1 to 8, from 1 to 7, from 1 to 6 (from 1 to several), from 1 to 5, from 1 to 4, from 1 to 3, from 1 to 2, or 1. A smaller number of deleted, substituted, inserted, and/or added amino acids is generally more preferable. Two or more different types of modifications selected from amino acid residue deletion, substitution, insertion, and addition may be carried out concurrently. Such regions can be obtained using site specific mutagenesis as described in, for example, MOLECULAR CLONING 3RD, CURRENT PROTOCOLS IN MOLECULAR BIOLOGY; *Nuc. Acids Res.*, 10, 6487 (1982); *Proc. Natl. Acad. Sci. USA*, 79, 6409 (1982); *Gene*, 34, 315 (1985); *Nuc. Acids Res.*, 13, 4431 (1985); *Proc. Natl. Acad. Sci. USA*, 82, 488 (1985).

In addition, the range denoted by "at least approximately 90%" in "a polypeptide including an amino acid sequence that has at least approximately 90% identity" is, for example, at least approximately 90%, at least approximately 91%, at least approximately 92%, at least approximately 93%, at least approximately 94%, at least approximately 95%, at least approximately 96%, at least approximately 97%, at least approximately 98%, at least approximately 99%, at least approximately 99.1%, at least approximately 99.2%, at least approximately 99.3%, at least approximately 99.4%, at least approximately 99.5%, at least approximately 99.6%, at least approximately 99.7%, at least approximately 99.8%, or at least approximately 99.9%. In general, larger numerical values for this identity are more preferable. Amino acid sequence identity and base sequence identity can be determined using analytical programs such as BLAST (refer, for example, to Altzshul S. F. et al., *J. Mol. Biol.* 215, 403 (1990)) or FASTA (refer, for example, to Pearson W. R., *Methods in Enzymology*, 183, 63 (1990)). The default parameters for the particular program are employed when BLAST or FASTA is used.

The polynucleotide that hybridizes under stringent conditions is described below.

The subscript n represents an integer from 1 to 5 wherein 2 or 3 is preferred and 2 is particularly preferred.

The individual Zs in the polypeptide represented by the formula $(Z)_n$ may be the same as each other or may differ from one another.

Polypeptide represented by the formula $(Z)_2$ is particularly preferred for the polypeptide represented by the formula $(Z)_n$.

Polypeptide represented by the formula $(Z)_2$ can be exemplified by a polypeptide including the amino acid sequence of SEQ ID NO: 3 and by a polypeptide that has substantially the same activity or function as a polypeptide including the amino acid sequence of SEQ ID NO: 3. In this Specification, a polypeptide including the amino acid sequence of SEQ ID NO: 3 and a polypeptide that has substantially the same activity or function as a polypeptide including the amino acid sequence of SEQ ID NO: 3 are referred to as the "ZZ domain."

Here, "substantially the same activity or function" means, for example, an activity or function that enables the fusion protein to be expressed as soluble protein when expression as a fusion protein with a target protein is effected. Such an activity or function, for example, the IgG binding capacity of the ZZ domain, can be measured by an IgG binding assay.

The polypeptide represented by $(Z)_2$ can be more specifically exemplified by polypeptide selected from the group of (e) a polypeptide including the amino acid sequence of SEQ ID NO: 3, (f) a polypeptide that includes an amino acid sequence with, in the amino acid sequence of SEQ ID NO: 3, one or more deleted, substituted, inserted and/or added amino acids, and that has the activity or function when expressed as a fusion protein with a target protein of enabling the fusion protein to be expressed as a soluble protein, (g) a polypeptide that includes an amino acid sequence having at least approximately 90% identity with the amino acid sequence of SEQ ID NO: 3, and that has the activity or function when expressed as a fusion protein with a target protein of enabling the fusion protein to be expressed as a soluble protein, and (h) a polypeptide including an amino acid sequence that is encoded by a polynucleotide that hybridizes under stringent conditions with a polynucleotide including a base sequence that is complementary to the base sequence of SEQ ID NO: 4, and having the activity or function when expressed as a fusion protein with a target protein of enabling the fusion protein to be expressed as a soluble protein.

The Target Protein

There are no particular limitations on the target protein in the fusion protein of the invention. For example, even proteins that are prone to form inclusion bodies when expressed in a recombinant protein expression system can be advantageously used.

The target protein in the invention can be exemplified by protein (viral antigen), e.g., coat protein, core protein, protease, reverse transcriptase, integrase, and so forth, encoded in the genome of a pathogenic virus, e.g., hepatitis B virus, hepatitis C virus, HIV, influenza, and so forth; the Fab and $(Fab)_2$ of antibodies; growth factors such as platelet-derived growth factor (PDGF), stem cell growth factor (SCF), hepatocyte growth factor (HGF), transforming growth factor (TGF), nerve growth factor (NGF), epidermal growth factor (EGF), fibroblast growth factor (FGF), insulin-like growth factor (IGF), and so forth; cytokines such as tumor necrosis factor, interferon, interleukin, and so forth; hematopoietic factors such as erythropoietin, granulocyte colony-stimulating factor, granulocyte-macrophage colony-stimulating factor, macrophage colony-stimulating factor, thrombopoietin, and so forth; peptide hormones such as luteinizing hormone-releasing hormone (LH-RH), thyrotropin-releasing hormone (TRH), insulin, somatostatin, growth hormone, prolactin, adrenocorticotropic hormone (ACTH), melanocyte-stimulating hormone (MSH), thyroid-stimulating hormone (TSH), luteinizing hormone (LH), follicle-stimulating hormone (FSH), vasopressin, oxytoxin, calcitonin, parathyroid hormone (PTH), glucagon, gastrin, secretin, pancreozymin, cholecystokinin, angiotensin, human placenta lactogen, human chorionic gonadotropin (HCG), cerulein, motilin, and so forth; analgesic peptides such as enkephalin, endorphin, dynorphin, kyotorphin, and so forth; enzymes such as superoxide dismutase (SOD), urokinase, tissue plasminogen activator (TPA), asparaginase, kallikrein, and so forth; peptide neurotransmitters such as bombesin, neutrotensin, bradykinin, substance P, and so forth; as well as albumin, collagen, proinsulin, renin, α1 antitrypsin, and so forth. However, the target protein is not limited to the foregoing.

The target protein may be an apoprotein, that is, the protein portion of a holoprotein. The apoproteins can be exemplified by apoRLBP (refer, for example, to *FEBS Lett.* 268, 287-290 (1990)), apoaequorin (refer, for example, to *Proc. Natl. Acad. Sci. USA,* 82, 3154-3158 (1985)), apoclytin (refer, for example, to *FEBS Lett.* 315, 343-346 (1993)), apomitrocomin (refer, for example, to *FEBS Lett.* 333, 301-305 (1993)), apoobelin (refer, for example, to *Gene,* 153, 273-274 (1995)), and so forth. The amino acid sequence of apoaequorin is shown by SEQ ID NO: 21.

The target protein may also be *Gaussia* luciferase (hGL) or the 19 kDa protein (KAZ) that is the catalytic unit of *Oplophorus* (shrimp) luciferase. The amino acid sequence of *Gaussia* luciferase (hGL) is shown by SEQ ID NO: 23. SEQ ID NO: 25 shows the amino acid sequence of the 19 kDa protein (KAZ) that is the catalytic unit of *Oplophorus* (shrimp) luciferase.

The target protein of the invention also encompasses variants of the aforementioned protein. These variants encompass, for example, a protein that has the same activity as the aforementioned protein and that includes an amino acid sequence with, in the amino acid sequence of the aforementioned protein, one or more deleted, substituted, inserted and/or added amino acids. Such protein can be exemplified by protein that has the same activity as the aforementioned protein and that includes an amino acid sequence with, in the amino acid sequence of the aforementioned protein, one or more deleted, substituted, inserted and/or added amino acids, for example, 1 to 100, 1 to 90, 1 to 80, 1 to 70, 1 to 60, 1 to 50, 1 to 40, 1 to 30, 1 to 20, 1 to 10, 1 to 9, 1 to 8, 1 to 7, 1 to 6 (1 to several), 1 to 5, 1 to 4, 1 to 3, 1 to 2, or 1 amino acid residue. A smaller number of amino acid residue deletions, substitutions, insertions, and/or additions is generally more preferred. Two or more different types of modifications selected from deletion, substitution, insertion, and addition may be carried out concurrently.

The target protein of the invention also encompasses "partial peptides" of the aforementioned protein. A partial peptide of the protein can be exemplified by a partial peptide including an amino acid sequence in which a portion of the amino acid sequence of the aforementioned protein runs uninterrupted, wherein the partial peptide preferably has the same activity as said protein. Such a partial peptide can be exemplified by a polypeptide that has an amino acid sequence including at least approximately 20 and preferably at least approximately 50 of the amino acid residues in the amino acid sequence of the aforementioned protein. This polypeptide preferably includes the amino acid sequence that corresponds to the region that is involved with the activity of the aforementioned protein. In addition, the partial peptide used in the invention may also be a partial peptide as yielded by a modification of this polypeptide wherein 1 or a plurality of amino acid residues (for example, approximately 1 to 20, more preferably approximately 1 to 10, and even more preferably approximately 1 to 5) is deleted from, substituted in, inserted into, and/or added to its amino acid sequence.

The partial peptide used in the invention can also be used as an antigen for antibody production.

The Cleavable Linker Peptide

The fusion protein of the invention can also include, between the first amino acid sequence including the amino acid sequence of the polypeptide represented by the formula $(Z)_n$ and the second amino acid sequence including the amino acid sequence of the target protein, an amino acid sequence including the amino acid sequence of a cleavable linker peptide.

This cleavable linker peptide denotes a linker peptide that has a cleavage site that can be cleaved by an enzymatic or chemical cleavage agent. A large number of peptides that can be cleaved by an enzyme (protease) or chemical are known (refer, for example, to Harlow and Lane, ANTIBODIES: A LABORATORY MANUAL, Cold Spring Harbor Laboratory Press, Cold Spring Harbor, N.Y. (1988); Walsh, PROTEINS: BIOCHEMISTRY AND BIOTECHNOLOGY, John Wiley & Sons, Ltd., West Sussex, England (2002)). A cleavage agent is a chemical or enzyme that recognizes a cleavage site in a peptide and that, by cleaving a bond within the peptide, splits the peptide into two peptides. The cleavage agent can be exemplified by chemicals and proteases.

A linker peptide that has a protease cleavage site is a preferred cleavable linker peptide for the invention. The protease cleavage site can be exemplified by the thrombin cleavage site, human rhinovirus 3C protease cleavage site, factor Xa cleavage site, and so forth.

When the fusion protein of the invention includes a cleavable linker peptide, the target protein, as yielded by the removal of the first amino acid sequence from the fusion protein of the invention, can be obtained by treatment with the cleavage agent after the fusion protein of the invention has been expressed.

The fusion protein of the invention can also be specifically exemplified by fusion protein represented by the formula $(Z)_n$-L-X, wherein L represents a direct bond or a cleavable linker peptide, X represents the amino acid sequence of a target protein, and n and Z are defined as above.

The fusion protein of the invention may further include a translation-enhancing amino acid sequence and/or an amino acid sequence that facilitates purification. The amino acid sequences used in this technical field can be used as the translation-enhancing amino acid sequence. The TEE sequence is an example of a translation-enhancing amino acid sequence. The amino acid sequences used in this technical field can be used as the amino acid sequence that facilitates purification. The purification-facilitating amino acid sequence can be, for example, a histidine tag sequence that has at least 4 and preferably at least 6 histidine residues in succession, the amino acid sequence for the glutathione-binding domain of glutathione S-transferase, and so forth. The purification-facilitating amino acid sequence is present preferably on the amino terminal side of the first amino acid sequence.

The Polynucleotide of the Invention

The invention also provides polynucleotide that codes for the above-described fusion protein of the invention. The polynucleotide of the invention may be any polynucleotide that includes a base sequence that codes for the fusion protein of the invention, and DNA is preferred. This DNA can be exemplified by genomic DNA, a genomic DNA library, cDNA of cellular or tissue origin, a cDNA library of cellular or tissue origin, synthetic DNA, and so forth. The vector used in such a library is not particularly limited and may be any one selected from, for example, bacteriophages, plasmids, cosmids, phagemids, and so forth. Amplification can also be carried out by the direct reverse transcription polymerase chain reaction (abbreviated below as the RT-PCR technique) using a total RNA or mRNA fraction prepared from the aforesaid cells or tissue.

The polynucleotide of the invention specifically encompasses a polynucleotide that includes:

(1) a first coding sequence including a polynucleotide coding for polypeptide that is represented by the formula $(Z)_n$ and that when expressed as a fusion protein with a target protein exhibits an activity or function whereby said fusion protein can be expressed as a soluble protein, and (2) a second coding sequence that includes a polynucleotide that codes for a target protein.

This formula $(Z)_n$ has the same definition as above.

Preferred as the polynucleotide of the invention is a polynucleotide that includes (1) a first coding sequence including a polynucleotide coding for polypeptide represented by the formula $(Z)_2$ and (2) a second coding sequence that includes a polynucleotide that codes for a target protein.

This formula $(Z)_2$ has the same definition as above.

The polynucleotide coding for a polypeptide represented by the formula $(Z)_2$ can be exemplified by a polynucleotide selected from the group of:

(e) a polynucleotide including a polynucleotide including g the base sequence of SEQ ID NO: 4, (f) a polynucleotide including a polynucleotide that hybridizes under stringent conditions with a polynucleotide including a base sequence complementary to the base sequence of SEQ ID NO: 4 and that codes for a polypeptide that when expressed as a fusion protein with a target protein exhibits an activity or function whereby said fusion protein can be expressed as a soluble protein, (g) a polynucleotide including a polynucleotide that codes for a polypeptide including the amino acid sequence of SEQ ID NO: 3, and (h) a polynucleotide including a polynucleotide coding for a polypeptide that includes an amino acid sequence with, in the amino acid sequence of SEQ ID NO: 3, one or more deleted, substituted, inserted and/or added amino acids and that when expressed as a fusion protein with a target protein exhibits an activity or function whereby said fusion protein can be expressed as a soluble protein.

Preferred polynucleotide of the invention of the type described above can be exemplified by a polynucleotide that include:

(1) a first coding sequence selected from the group of:
(e) a polynucleotide including a polynucleotide including the base sequence of SEQ ID NO: 4,
(f) a polynucleotide including a polynucleotide that hybridizes under stringent conditions with a polynucleotide including a base sequence complementary to the base sequence of SEQ ID NO: 4 and that codes for a polypeptide that when expressed as a fusion protein with a target protein exhibits an activity or function whereby said fusion protein can be expressed as a soluble protein,
(g) a polynucleotide including a polynucleotide that codes for a polypeptide including the amino acid sequence of SEQ ID NO: 3, and
(h) a polynucleotide including a polynucleotide coding for a polypeptide that includes an amino acid sequence with, in the amino acid sequence of SEQ ID NO: 3, one or more deleted, substituted, inserted and/or added amino acids and that when expressed as a fusion protein with a target protein exhibits an activity or function whereby said fusion protein can be expressed as a soluble protein; and (2) a second coding sequence including a polynucleotide coding for a target protein.

Here, a "polynucleotide that hybridizes under stringent conditions (for example, DNA)" denotes polynucleotide (for example, DNA) obtained using, for example, the colony hybridization method, plaque hybridization method, or Southern hybridization method, employing as a probe all or a portion of a polynucleotide including a base sequence complementary to the base sequence of SEQ ID NO: 2 or SEQ ID NO: 4 or all or a portion of a polynucleotide coding for the amino acid sequence in SEQ ID NO: 1 or SEQ ID NO: 3. A specific example is the polynucleotide immobilized by the following procedure: hybridization at 65° C. in the presence of 0.7 to 1.0 mol/L NaCl using a filter on which polynucleotide of colony or plaque origin has been immobilized, followed by washing the filter at 65° C. using 0.1× to 2× saline-sodium citrate (SSC) solution (the 1×SSC solution includes 150 mmol/L sodium chloride and 15 mmol/L sodium citrate).

Hybridization can be carried out in accordance with the methods described in such laboratory manuals as Sambrook J. et al., MOLECULAR CLONING: A LABORATORY MANUAL, Third Edition, Cold Spring Harbor Laboratory Press (2001) (abbreviated below as MOLECULAR CLONING (3RD)); Ausbel F. M. et al., CURRENT PROTOCOLS IN MOLECULAR BIOLOGY, Supplements 1-38, John Wiley and Sons (1987-1997); Glover D. M. and Hames B. D., DNA CLONING 1: CORE TECHNIQUES, A PRACTICAL APPROACH, Second Edition, Oxford University Press (1995), and so forth.

The "stringent conditions" cited in this Specification may be low-stringency conditions, medium-stringency conditions, or high-stringency conditions. "Low-stringency conditions" denote, for example, 5×SSC, 5×Denhardt solution, 0.5% (w/v) SDS, 50% (v/v) formamide, and 32° C. "Medium-stringency conditions" denote, for example, 5×SSC, 5×Denhardt solution, 0.5% (w/v) SDS, 50% (v/v) formamide, and 42° C. "High-stringency conditions" denote, for example, 5×SSC, 5×Denhardt solution, 0.5% (w/v) SDS, 50% (v/v) formamide, and 50° C. More severe conditions require a higher degree of complementarity to form the double strand. Specifically, it can be expected that, for example, under these conditions polynucleotide (for example, DNA) having a higher degree of complementarity will be efficiently obtained at higher temperatures. However, a number of factors, such as temperature, probe concentration, probe length, ionic strength, temperature, salt concentration, and so forth, can be viewed as factors that influence the stringency of the hybridization, and the individual skilled in the art will be able to effect the same stringency by an appropriate selection of these factors.

An example of a commercial kit that can be used for hybridization is the Alkphos direct labeling reagents (Amersham Pharmacia). In this case, in accordance with the protocol provided with the kit, incubation can be carried out overnight with the labeled probes, followed by washing the membrane at 55° C. with the primary wash buffer containing 0.1% (w/v) SDS and detection of the hybridized DNA.

In addition to the preceding, other examples of hybridizable polynucleotides are DNA having approximately at least a 60%, at least a 65%, at least a 70%, at least a 75%, at least an 80%, at least an 85%, at least an 88%, at least a 90%, at least a 92%, at least a 95%, at least a 97%, at least a 98%, at least a 99%, at least a 99.3%, at least a 99.5%, at least a 99.7%, at least a 99.8%, or at least a 99.9% identity, as calculated with an analytical program such as FASTA or BLAST using the default parameters therefor, with polynucleotide coding for the amino acid sequence of SEQ ID NO: 1 or SEQ ID NO: 3. The identity of amino acid sequences or base sequences can be determined using the methodology described above.

Polynucleotide coding for a region that has an amino acid sequence generated by subjecting a certain amino acid sequence, one or more deleted, substituted, inserted and/or added amino acids, can be obtained using site specific mutagenesis methods (refer, for example, to Gotoh, T. et al., *Gene,* 152, 271-275 (1995); Zoller, M. J., and Smith, M., *Methods Enzymol.,* 100, 468-500 (1983); Kramer, W. et al., *Nucleic Acids Res.,* 12, 9441-9456 (1984); Kramer, W., and Fritz, H. J., *Methods Enzymol.,* 154, 350-367 (1987); Kunkel, T. A., *Proc. Natl. Acad. Sci. USA,* 82, 488-492 (1985); and Kunkel, *Methods Enzymol.,* 85, 2763-2766 (1988)), methods that employ the amber mutation (for example, the gapped duplex method, refer, for example, to *Nucleic Acids Res.,* 12, 9441-9456 (1984)), and so forth.

Mutations can also be introduced into a polynucleotide by PCR that uses a primer set having at each 5' end a sequence into which the desired mutation (deletion, addition, substitution, and/or insertion) has been introduced (refer, for example, to Ho S. N. et al., *Gene,* 77, 51 (1989)).

Polynucleotides coding for a fragment of a protein that is a type of deletion mutant can be acquired by PCR using polynucleotides coding for the protein as the template and using the following primers: an oligonucleotide that has a sequence that matches the 5' end base sequence of the region coding for the target fragment in the polynucleotide that codes for the protein, and an oligonucleotide that has a sequence complementary to the 3' end base sequence.

Polynucleotide of the invention can be specifically exemplified by a polynucleotide including a polynucleotide coding for a fusion protein including the amino acid sequence of SEQ ID NO: 7, SEQ ID NO: 11, SEQ ID NO: 15, SEQ ID NO: 17, or SEQ ID NO: 19. Polynucleotide including a polynucleotide including the base sequence described in SEQ ID NO: 8 is an example of polynucleotide including a polynucleotide that codes for a fusion protein including the amino acid sequence described in SEQ ID NO: 7. Polynucleotide including a polynucleotide including the base sequence described in SEQ ID NO: 12 is an example of polynucleotide including a polynucleotide that codes for a fusion protein including the amino acid sequence described in SEQ ID NO: 11. Polynucleotide including a polynucleotide including the base sequence described in SEQ ID NO: 16 is an example of polynucleotide including a polynucleotide that codes for a fusion protein including the amino acid sequence described in SEQ ID NO: 15. Polynucleotide including a polynucleotide including the base sequence described in SEQ ID NO: 18 is an example of polynucleotide including a polynucleotide that codes for a fusion protein including the amino acid sequence described in SEQ ID NO: 17. Polynucleotide including a polynucleotide including the base sequence described in SEQ ID NO: 20 is an example of polynucleotide including a polynucleotide that codes for a fusion protein including the amino acid sequence described in SEQ ID NO: 19.

Polynucleotide of the invention may further include, between the aforementioned first coding sequence and the aforementioned second coding sequence, a polynucleotide coding for a cleavable linker peptide. The cleavable linker peptide is in accordance with that already described above.

Polynucleotide of the invention may additionally incorporate polynucleotide (coding sequence) including a polynucleotide coding for a translation-enhancing amino acid sequence and/or polynucleotide (coding sequence) including a polynucleotide coding for a purification-facilitating amino acid sequence. Polynucleotide including a polynucleotide coding for a translation-enhancing amino acid sequence as used in this technical field can be used for the polynucleotide including a polynucleotide coding for a translation-enhancing amino acid sequence. The translation-enhancing amino acid sequence can be exemplified by those previously cited. Polynucleotide including a polynucleotide coding for a purification-facilitating amino acid sequence as used in this technical field can be used for the polynucleotide coding for a purification-facilitating amino acid sequence. The purification-facilitating amino acid sequence can be exemplified by those previously cited. The polynucleotide (coding sequence) including a polynucleotide coding for a purification-facilitating amino acid sequence is preferably present on the 5' side of the first coding sequence.

The Expression Vector and Transformants of the Invention

The invention additionally provides an expression vector including the above-described polynucleotide of the invention and also provides transformants.

The Expression Vector

The expression vector of the invention can be obtained by the ligation (insertion) of a polynucleotide (DNA) of the invention into a suitable vector. More specifically, the expression vector of the invention can be obtained by cleavage of the purified polynucleotide (DNA) with a suitable restriction enzyme and ligation into a suitable vector by insertion into the restriction enzyme site or a multicloning site on the vector.

The expression vector of the invention can be specifically exemplified by an expression vector including:

(1) an expression-inducible promoter sequence;

(2) a first coding sequence including a polynucleotide coding for a polypeptide that is represented by the formula $(Z)_n$, wherein n and Z have the same definitions as above, and that when expressed as a fusion protein with a target protein has the function of enabling the fusion protein to be expressed as a soluble protein; and (3) a second coding sequence that includes a polynucleotide that codes for a target protein.

The vector for insertion of the polynucleotide of the invention is not particularly limited as long as it has the capacity to replicate in the host, and can be exemplified by plasmids, bacteriophages, animal viruses, and so forth. The plasmids can be exemplified by plasmids originating from *Escherichia coli* (e.g., pBR322, pBR325, pUC118, pUC119, and so forth), plasmids originating from *Bacillus subtilis* (e.g., pUB110, pTP5, and so forth), plasmids originating from yeast (e.g., YEp13, YEp24, YCp50, and so forth), and so forth. The bacteriophages can be exemplified by λ phage and so forth. The animal viruses can be exemplified by retroviruses, vaccinia viruses, insect viruses (e.g., baculoviruses), and so forth. In addition, the pCold I vector, pCold II vector, pCold III vector, and pCold IV vector (all of these are products of Takara Bio Inc.) can also be very suitably used.

The polynucleotide is generally ligated in an expressible manner downstream from a promoter (the expression-inducible promoter) in a suitable vector. When the host at the time of transformation is an animal cell, the promoter used is preferably an SV40-derived promoter, retrovirus promoter, metallothionein promoter, heat shock promoter, cytomegalovirus promoter, SRα promoter, and so forth. When the host is an *Escherichia* species, the Trp promoter, T7 promoter, lac promoter, recA promoter, λPL promoter, lpp promoter, and so forth are preferred. When the host is a *Bacillus* species, the SPO1 promoter, SPO2 promoter, penP promoter, and so forth are preferred. When the host is a yeast, the PHO5 promoter, PGK promoter, GAP promoter, ADH1 promoter, GAL promoter, and so forth are preferred. When the host is an insect cell, the polyhedrin promoter, P10 promoter, and so forth are preferred. A low-temperature expression-inducible promoter is also very suitably used. Low-temperature expression-inducible promoters can be exemplified by the promoter sequences for cold shock genes. The cold shock gene can be exemplified by *Escherichia coli* cold shock genes (e.g., cspA, cspB, cspG; cspI, csdA, and so forth), *Bacillus caldolyticus* cold shock genes (e.g., Bc-Csp and so forth), *Salmonella enterica* cold shock genes (e.g., cspE and so forth), and *Erwinia carotovora* cold shock genes (e.g., cspG and so forth). Very suitable thereamong for use as the low-temperature expression-inducible promoter are, for example, the cspA promoter, cspB promoter, cspG promoter, cspI promoter, and csdA promoter.

In addition to the preceding, the expression vector of the invention may as desired include an enhancer, splicing signal, polyA addition signal, ribosome binding sequence (SD sequence), selection marker, and so forth. The selection marker can be exemplified by the dihydrofolate reductase gene, ampicillin resistance gene, neomycin resistance gene, and so forth.

The expression vector of the invention may also incorporate a polynucleotide including a base sequence that encodes a translation-enhancing amino acid sequence and/or a polynucleotide including a base sequence that encodes a purification-facilitating amino acid sequence. Polynucleotide including a base sequence that encodes a translation-enhancing amino acid sequence as used in this technical field can be used for the polynucleotide including a base sequence that encodes a translation-enhancing amino acid sequence. The translation-enhancing amino acid sequence can be exemplified by those previously cited. Polynucleotide including a base sequence that encodes a purification-facilitating amino acid sequence as used in this technical field can be used for the polynucleotide that encodes a purification-facilitating amino acid sequence. The purification-facilitating amino acid sequence can be exemplified by those previously cited.

The Transformants

A transformant can be constructed by transfecting a suitable host with an expression vector, obtained proceeding as above, that includes a polynucleotide of the invention (that is, a polynucleotide coding for a fusion protein of the invention). There is no particular limitation on the host as long as it is capable of expressing the polynucleotide (DNA) of the invention. The host can be exemplified by *Escherichia* species, *Bacillus* species, *Pseudomonas* species, *Rhizobium* species, yeast, animal cells, and insect cells. The *Escherichia* species can be exemplified by *Escherichia coli*; the *Bacillus* species can be exemplified by *Bacillus subtilis*; the *Pseudomonas* species can be exemplified by *Pseudomonas putida*; the *Rhizobium* species can be exemplified by *Rhizobium meliloti*; the yeast species can be exemplified by *Saccharomyces cerevisiae* and *Schizosaccharomyces pombe*; the animal cells can be exemplified by COS cells and CHO cells; and the insect cells can be exemplified by Sf9 and Sf21.

The method of transfecting the expression vector into the host and the method of transformation thereby can follow the various general methods. The method of transfecting the expression vector into the host cell can be exemplified by the calcium phosphate method (*Virology*, 52, 456-457 (1973)), the lipofection method (*Proc. Natl. Acad. Sci. USA*, 84, 7413 (1987)), the electroporation method (*EMBO J.*, 1, 841-845 (1982)), and so forth. The transformation method for *Escherichia* species can be exemplified by the methods described in *Proc. Natl. Acad. Sci. USA*, 69, 2110 (1972) and *Gene*, 17, 107 (1982). The transformation method for *Bacillus* species can be exemplified by the method described in *Molecular & General Genetics*, 168, 111 (1979). The method for transforming yeast can be exemplified by the method described in *Proc. Natl. Acad. Sci. USA*, 75, 1929 (1978). The method for transforming animal cells can be exemplified by the method described in *Virology*, 52, 456 (1973). The method for transforming insect cells can be exemplified by the method described in *Bio/Technology*, 6, 47-55 (1988). Proceeding in this manner, a transformant can be obtained that has been transformed by an expression vector including polynucleotide (the polynucleotides of the invention) that code for fusion protein of the invention.

The Expression Vector Including a Low-Temperature Expression-Inducible Promoter Sequence and Transformants Among the preceding, an expression vector that includes a low-temperature expression-inducible promoter sequence is preferred for the expression vector of the invention. The fusion protein of the invention can be expressed as a soluble protein by using an expression vector that includes a low-temperature expression-inducible promoter sequence.

This expression vector that includes a low-temperature expression-inducible promoter sequence specifically denotes an expression vector that includes (1) a low-temperature expression-inducible promoter sequence;

(2) a first coding sequence including a polynucleotide coding for a polypeptide that is represented by the formula $(Z)_n$, wherein n and Z are defined as above, and that has the activity or function when expressed as a fusion protein with a target protein of enabling the fusion protein to be expressed as a soluble protein; and (3) a second coding sequence that includes a polynucleotide that codes for a target protein.

The polypeptide that is represented by formula $(Z)_n$ is in accordance with the description provided above.

Among the preceding, an expression vector that includes (1) a low-temperature expression-inducible promoter sequence;

(2) a first coding sequence including a polynucleotide coding for a polypeptide that is represented by the formula $(Z)_2$, wherein Z is defined as above; and (3) a second coding sequence that includes a polynucleotide that codes for a target protein, is preferred for the expression vector that includes a low-temperature expression-inducible promoter sequence.

The polypeptide that is represented by formula $(Z)_2$ is in accordance with the description provided above.

The polynucleotide coding for a polypeptide that is represented by formula $(Z)_2$ is in accordance with the description provided above.

The low-temperature expression-inducible promoter sequence denotes a promoter sequence of which expression of the target protein can be induced by lowering the temperature from the culture conditions that cause host cell growth. Examples of low-temperature expression-inducible promoters are the promoters for genes that code for cold shock proteins (cold shock genes). Cold shock gene promoters can be exemplified by the cold shock gene promoters from *Escherichia coli*, the cold shock gene promoters from *Bacillus caldolyticus* (for example, Bc-Csp), the cold shock gene promoters from *Salmonella enterica* (for example cspE), and the cold shock gene promoters from *Erwinia carotovora* (for example, cspG). The cold shock gene promoters from *Escherichia coli* can be exemplified by the cspA promoter, cspB promoter, cspG promoter, cspI promoter, csdA promoter, and so forth, wherein the cspA promoter is preferred. The cold shock gene promoters from *Bacillus caldolyticus* can be exemplified by Bc-Csp and so forth. The cold shock gene promoters from *Salmonella enterica* can be exemplified by cspE and so forth. The cold shock gene promoters from *Erwinia carotovora* can be exemplified by cspG and so forth.

The temperature at which expression driven by the low-temperature expression-inducible promoter used by the invention can be induced is generally 30° C. or less, preferably 25° C. or less, more preferably 20° C. or less, and particularly preferably 15° C. or less. However, because the expression efficiency declines at excessively low temperatures, expression is induced generally at 5° C. or more, preferably at 10° C. or more, and particularly preferably at approximately 15° C.

For example, the pCold I vector, pCold II vector, pCold III vector, and pCold IV vector (all of these are products of Takara Bio Inc.) can be very suitably used as the vector for insertion of the polynucleotide of the invention when it is desired to construct an expression vector according to the invention that contains a low-temperature expression-inducible promoter sequence. The fusion protein of the invention can be prepared as a soluble protein in the cytoplasm of the host cell when expression is carried out in a prokaryotic host cell using these vectors.

Prokaryotic cells are preferred for the host for transfection with an expression vector according to the invention that includes a low-temperature expression-inducible promoter sequence, with *Escherichia coli* being preferred and the BL21 strain and JM109 strain being particularly preferred, wherein the BL21 strain is preferred between the two.

Temperatures generally of 25° C. to 40° C. and preferably of 30° C. to 37° C. are used for cultivation temperature for bringing about cell proliferation of the transformant that has been transfected with an expression vector according to the invention that includes a low-temperature expression-inducible promoter sequence. The temperature for expression induction is generally 4° C. to 25° C., preferably 10° C. to 20° C., more preferably 12° C. to 18° C., and particularly preferably 15° C.

The expression vector of the invention also encompasses an expression vector that includes (1) an expression-inducible promoter sequence;
(2) a first coding sequence including a polynucleotide coding for a polypeptide that is represented by the formula $(Z)_n$, wherein n and Z are defined as above, and that has the activity or function when expressed as a fusion protein with a target protein of enabling the fusion protein to be expressed as a soluble protein; and
(3) at least one restriction enzyme site that enables the insertion of a second coding sequence that includes a polynucleotide that codes for a target protein.

The expression-inducible promoter is preferably a low-temperature expression-inducible promoter.

The polypeptide represented by the formula $(Z)_n$ is in accordance with the description provided above.

The "at least one restriction enzyme site that enables the insertion of a second coding sequence that includes a polynucleotide that codes for a target protein" is a polynucleotide that includes a polynucleotide that has a restriction enzyme recognition site that enables the insertion of a second coding sequence that includes a polynucleotide that codes for a target protein. There are no particular restrictions on this restriction enzyme site as long as it enables the insertion of the second coding sequence that includes a polynucleotide that codes for a target protein, and it is preferably a so-called multicloning site. Restriction enzyme sites such as multicloning sites are well known in this technical field and have been reported (for example, Yanisch-Perron, C., Vieira, J. and Messing, J. *Gene*, 33, 103-119 (1985), Improved M13 phage cloning vectors and host strains: Nucleotide sequences of the M13mp18 and pUC19 vectors, *Gene*, 33, 103-119 (1985), and so forth).

An expression vector capable of expressing fusion protein of the invention can be prepared by ligating (inserting) the aforementioned polynucleotide that codes for a target protein into the subject expression vector's (3) at least one restriction enzyme site that enables the insertion of a second coding sequence that includes a polynucleotide that codes for a target protein.

A preferred expression vector of this type is an expression vector that includes (1) a low-temperature expression-inducible promoter sequence;
(2) a first coding sequence including a polynucleotide coding for a polypeptide that is represented by the formula $(Z)_2$ (wherein Z is defined as above); and
(3) at least one restriction enzyme site that enables the insertion of a second coding sequence that includes a polynucleotide that codes for a target protein.

The polypeptide represented by the formula $(Z)_2$ is in accordance with the description provided above.

The polynucleotide coding for polypeptide represented by the formula $(Z)_2$ is in accordance with the description provided above.

Polynucleotide coding for a cleavable linker peptide may additionally be present between the first coding sequence and the aforementioned at least one restriction enzyme site. This cleavable linker peptide is in accordance with the description already provided above.

A coding sequence including a polynucleotide that codes for a purification-facilitating amino acid sequence may also be present on the 5' side of the first coding sequence. This purification-facilitating amino acid sequence is in accordance with the description provided above.

Production of Fusion Protein of the Invention

The invention additionally provides a method of producing fusion protein of the invention, including a step of producing fusion protein of the invention by culturing a transformant as described above. Fusion protein of the invention can be prepared by forming and/or accumulating the fusion protein of the invention by culturing this transformant under conditions that enable the expression of the polynucleotide (DNA) coding for fusion protein of the invention, and then separating and/or purifying the fusion protein of the invention.

Cultivation of the Transformant

Cultivation of the transformant of the invention can be carried out according to the usual methods used for host cultivation. By means of this cultivation, fusion protein of the invention is formed by the transformant and accumulates within the transformant or in the culture medium.

The medium for cultivation of the transformant when an *Escherichia* or *Bacillus* species is used as the host may be any natural or synthetic medium that includes the carbon source, nitrogen source, inorganic salts, and so forth required for the growth of the transformant and that enables efficient cultivation of the transformant. The following can be used as the carbon source: carbohydrates such as glucose, fructose, sucrose, starch, and so forth; organic acids such as acetic acid, propionic acid, and so forth; and alcohols such as ethanol, propanol, and so forth. The following, for example, can be used as the nitrogen source: ammonia; the ammonium salts of inorganic and organic acids, e.g., ammonium chloride, ammonium sulfate, ammonium acetate, ammonium phosphate, and so forth; other nitrogenous compounds; as well as peptone, meat extract, corn steep liquor, and so forth. The following, for example, can be used as the inorganic salt: monopotassium phosphate, dipotassium phosphate, magnesium phosphate, magnesium sulfate, sodium chloride, ferrous sulfate, manganese sulfate, copper sulfate, and calcium carbonate. As necessary, an antibiotic, such as ampicillin or tetracycline, may be added to the medium during cultivation. In the case of the cultivation of a transformant that has been transformed with an expression vector that uses an inducible promoter for the promoter, the inducer may as necessary be added to the medium. For example, isopropyl-β-D-thiogalactopyranoside (IPTG) may be added to the medium in the case of the cultivation of a transformant that has been transformed with an expression vector that uses the Lac promoter, while indoleacetic acid (IAA) may be added to the medium in the case of the cultivation of a transformant that has been transformed with an expression vector that uses the trp promoter.

When the host is an *Escherichia* species, cultivation is generally carried out at about 15° C. to 43° C. for approximately 3 to approximately 24 hours, as necessary with the addition of aeration and/or stirring. When the host is a *Bacillus* species, cultivation is generally carried out at about 30° C. to 40° C. for approximately 6 to approximately 24 hours, as necessary with the addition of aeration and/or stirring.

The medium for cultivation of the transformant when the host is a yeast can be exemplified by Burkholder minimal medium (*Proc. Natl. Acad. Sci. USA*, 77, 4504 (1980)) and SD medium including 0.5% (w/v) casamino acids (*Proc. Natl. Acad. Sci. USA*, 81, 5330 (1984)). The pH of the medium is preferably adjusted to approximately 5 to approximately 8. Cultivation is generally carried out at approximately 20° C. to 35° C. for approximately 24 to approximately 72 hours, as necessary with the addition of aeration and/or stirring.

The medium for cultivation of the transformant when the host is an animal cell can be exemplified by MEM medium including approximately 5 to approximately 20% (v/v) fetal bovine serum (*Science*, 122, 501 (1952)) and DMEM medium (*Virology*, 8, 396 (1959)). The pH is preferably approximately 6 to approximately 8. Cultivation is generally carried out at approximately 30° C. to 40° C. for approximately 15 to approximately 60 hours, as necessary with the addition of aeration and/or stirring.

The medium for cultivation of the transformant when the host is an insect cell is preferably medium obtained by the suitable addition of additives, such as inactivated 10% (v/v) bovine serum and so forth, to Grace's insect medium (*Nature*, 195, 788 (1962)). The pH of the medium is preferably adjusted to approximately 6.2 to approximately 6.4. Cultivation is generally carried out at approximately 27° C. for approximately 3 to approximately 5 days, as necessary with the addition of aeration and/or stirring.

In those instances where the transformant of the invention has been transfected with an expression vector that incorporates a low-temperature expression-inducible promoter sequence, the cultivation temperature for carrying out cell proliferation of the transformant and the temperature for induction of expression are in accordance with that described previously.

Separation and/or Purification of the Fusion Protein of the Invention

The fusion protein of the invention can be obtained by separation and/or purification of the fusion protein of the invention from the above-described culture material. Here, the culture material refers to culture fluid and cultured microorganisms or cultured cells or to the disruptate from the cultured microorganisms or cultured cells. Separation and/or purification of the fusion protein of the invention can be carried out according to the usual methods.

In specific terms, when the fusion protein of the invention has accumulated within the cultured microorganism or cultured cells, cultivation can be followed by disruption of the microorganism or cells by the usual methods (for example, ultrasonic waves, lysozyme, freeze-thaw cycling, and so forth), after which a crude extract of the fusion protein of the invention can be obtained by the usual methods (for example, centrifugal separation, filtration, and so forth). When the fusion protein of the invention has accumulated in the periplasmic space, an extract containing the target protein can be obtained by the usual methods (for example, osmotic pressure shock and so forth) after the completion of cultivation. When the fusion protein of the invention accumulates in the culture fluid, after the completion of cultivation a culture supernatant including the fusion protein of the invention can be obtained by separation of the microorganism or cells and a culture supernatant by the usual methods (for example, centrifugal separation, filtration, and so forth).

Purification of the fusion protein of this invention present in the extract or culture supernatant obtained as described above can be carried out by the usual methods of separation and/or purification. For example, the following can be used, either singly or in a suitable combination, for the separation and/or purification procedure: ammonium sulfate precipitation, gel filtration chromatography, ion-exchange chromatography, affinity chromatography, reverse-phase high-performance liquid chromatography, dialysis, ultrafiltration, and so forth. Purification is preferably carried out using the above-described purification-facilitating amino acid sequence in those instances where the fusion protein of the invention includes a purification-facilitating amino acid sequence. Specifically, when the fusion protein of the invention includes a histidine tag sequence, nickel chelate affinity chromatography can be used, while affinity chromatography based on a glutathione-bonded gel can be used when the domain of glutathione S-transferase that binds to glutathione is present.

The descriptions in this Specification make the object, characteristic features, advantages, and idea of the invention clear to the individual skilled in the art, and the individual skilled in the art will be able to readily carry out the invention based on the descriptions in the Specification. The preferred embodiments and specific examples provide preferred modes for executing the invention and are given for purposes of illustration and explanation, and the invention is not limited to these. Various modifications that are within the meaning and scope of the invention as disclosed in this Specification will be clear to the individual skilled in the art based on the description of this Specification.

Sequence numbers in the Sequence Listing of the specification indicate the following sequences:

SEQ ID NO: 1 shows the amino acid sequence of a polypeptide represented by the formula Z.

SEQ ID NO: 2 shows the base sequence of DNA that encodes the amino acid sequence shown by SEQ ID NO: 1.

SEQ ID NO: 3 shows the amino acid sequence of a polypeptide represented by the formula $(Z)_2$.

SEQ ID NO: 4 shows the base sequence of DNA that encodes the amino acid sequence shown by SEQ ID NO: 3.

SEQ ID NO: 5 shows the amino acid sequence of recombinant apoaequorin that is encoded by DNA inserted into the apoaequorin expression vector pCold-AQ constructed in Reference Example 1.

SEQ ID NO: 6 shows the base sequence of DNA that encodes recombinant apoaequorin and that is inserted into the apoaequorin expression vector pCold-AQ constructed in Reference Example 1.

SEQ ID NO: 7 shows the amino acid sequence of recombinant ZZ-apoaequorin fusion protein that is encoded by DNA inserted into the ZZ-apoaequorin fusion protein expression vector pCold-ZZ-AQ constructed in Example 1.

SEQ ID NO: 8 shows the base sequence of DNA that encodes recombinant ZZ-apoaequorin fusion protein and that is inserted into the ZZ-apoaequorin fusion protein expression vector pCold-ZZ-AQ constructed in Example 1.

SEQ ID NO: 9 shows the amino acid sequence of recombinant *Gaussia* luciferase that is encoded by DNA inserted into the *Gaussia* luciferase expression vector pCold-hGL constructed in Reference Example 2.

SEQ ID NO: 10 shows the base sequence of DNA that encodes recombinant *Gaussia* luciferase and that is inserted into the *Gaussia* luciferase expression vector pCold-hGL constructed in Reference Example 2.

SEQ ID NO: 11 shows the amino acid sequence of recombinant ZZ-*Gaussia* luciferase fusion protein that is encoded by DNA inserted in the ZZ-*Gaussia* luciferase fusion protein expression vector pCold-ZZ-hGL constructed in Example 2.

SEQ ID NO: 12 shows the base sequence of DNA that encodes recombinant ZZ-*Gaussia* luciferase fusion protein and that is inserted into the ZZ-*Gaussia* luciferase fusion protein expression vector pCold-ZZ-hGL constructed in Example 2.

SEQ ID NO: 13 shows the amino acid sequence of recombinant KAZ (the 19 kDa protein that is the catalytic unit of *Oplophorus* (shrimp) luciferase) that is encoded by DNA inserted in the KAZ expression vector pCold-KAZ constructed in Reference Example 3.

SEQ ID NO: 14 shows the base sequence of DNA that encodes recombinant KAZ (the 19 kDa protein that is the catalytic unit of *Oplophorus* (shrimp) luciferase) and that is inserted into the KAZ expression vector pCold-KAZ constructed in Reference Example 3.

SEQ ID NO: 15 shows the amino acid sequence of recombinant ZZ-KAZ fusion protein that is encoded by DNA inserted in the ZZ-KAZ fusion protein expression vector pCold-ZZ-KAZ constructed in Example 3.

SEQ ID NO: 16 shows the base sequence of DNA that encodes recombinant ZZ-KAZ fusion protein and that is inserted in the ZZ-KAZ fusion protein expression vector pCold-ZZ-KAZ constructed in Example 3.

SEQ ID NO: 17 shows the amino acid sequence of recombinant ZZ-*Gaussia* luciferase fusion protein that is encoded by DNA inserted into pCold-ZZ-T-hGL, an expression vector constructed in Example 4 for ZZ-*Gaussia* luciferase fusion protein that has a thrombin cleavage site.

SEQ ID NO: 18 shows the base sequence of DNA that encodes recombinant ZZ-*Gaussia* luciferase fusion protein and that is inserted into pCold-ZZ-T-hGL, an expression vector constructed in Example 4 for ZZ-*Gaussia* luciferase fusion protein that has a thrombin cleavage site.

SEQ ID NO: 19 shows the amino acid sequence of recombinant ZZ-*Gaussia* luciferase fusion protein that is encoded by DNA inserted into pCold-ZZ-P-hGL, an expression vector constructed in Example 4 for ZZ-*Gaussia* luciferase fusion protein that has a human rhinovirus 3C protease cleavage site.

SEQ ID NO: 20 shows the base sequence of DNA that encodes recombinant ZZ-*Gaussia* luciferase fusion protein and that is inserted into pCold-ZZ-P-hGL, an expression vector constructed in Example 4 for ZZ-*Gaussia* luciferase fusion protein that has a human rhinovirus 3C protease cleavage site.

SEQ ID NO: 21 shows the amino acid sequence of apoaequorin.

SEQ ID NO: 22 shows the base sequence of DNA that codes for apoaequorin.

SEQ ID NO: 23 shows the amino acid sequence of *Gaussia* luciferase.

SEQ ID NO: 24 shows the base sequence of DNA that codes for *Gaussia* luciferase.

SEQ ID NO: 25 shows the amino acid sequence of the 19 kDa protein (KAZ) that is the catalytic unit of *Oplophorus* (shrimp) luciferase.

SEQ ID NO: 26 shows the base sequence of DNA that codes for the 19 kDa protein (KAZ) that is the catalytic unit of *Oplophorus* (shrimp) luciferase.

SEQ ID NO: 27 shows the base sequence of a primer used in Reference Example 1.

SEQ ID NO: 28 shows the base sequence of a primer used in Reference Example 1.

SEQ ID NO: 29 shows the base sequence of a primer used in Example 1.

SEQ ID NO: 30 shows the base sequence of a primer used in Example 1.

SEQ ID NO: 31 shows the base sequence of a primer used in Reference Example 2.

SEQ ID NO: 32 shows the base sequence of a primer used in Reference Example 2.

SEQ ID NO: 33 shows the base sequence of a primer used in Example 2.

SEQ ID NO: 34 shows the base sequence of a primer used in Example 2.

SEQ ID NO: 35 shows the base sequence of a primer used in Reference Example 3.

SEQ ID NO: 36 shows the base sequence of a primer used in Reference Example 3.

SEQ ID NO: 37 shows the base sequence of a primer used in Example 3.

SEQ ID NO: 38 shows the base sequence of a primer used in Example 3.

SEQ ID NO: 39 shows the base sequence of a thrombin cleavage recognition sequence oligonucleotide used in Example 4.

SEQ ID NO: 40 shows the base sequence of a thrombin cleavage recognition sequence oligonucleotide used in Example 4.

SEQ ID NO: 41 shows the base sequence of a human rhinovirus 3C protease cleavage recognition sequence oligonucleotide used in Example 4.

SEQ ID NO: 42 shows the base sequence of a human rhinovirus 3C protease cleavage recognition sequence oligonucleotide used in Example 4.

EXAMPLES

Examples are given below to more fully illustrate the invention, and should not be construed as limiting the invention.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

Reference Example 1

Construction of an apoAQ expression vector (pCold-AQ)

The aequorin gene coding for the calcium-binding photoprotein apoaequorin (apoaequorin is abbreviated below as "apoAQ") was prepared by PCR from pAM-HE containing a HindIII-EcoRI fragment that was the coding region of pAQ440 (Japanese Patent Application Laid-open No. S 61-135586). The pCold II vector (Takara Bio Inc.) was used as the expression vector.

Using pAM-HE as the template and the two PCR primers AQ-EcoRI-Met (5' ccg GAATTC ATG AAA CTT ACA TCA GAC TTC GAC AAC 3' (SEQ ID NO: 27); the EcoRI restriction enzyme site is underlined) and AQ-C-SalI (5' cgc GTCGAC TTA GGG GAC AGC TCC ACC GTA GAG CTT 3' (SEQ ID NO: 28); the SalI restriction enzyme site is underlined), the desired aequorin gene region was amplified by PCR (25 cycles, cycle conditions: 1 minute/94° C., 1 minute/50° C., 1 minute/72° C.) using a PCR kit (Takara Bio Inc.). The obtained DNA fragments were purified with a PCR purification kit (Qiagen). The purified DNA fragments were digested by the usual method with the restriction enzymes EcoRI/SalI and were thereafter ligated into the EcoRI/SalI restriction enzyme sites of pCold II to construct the pCold-AQ expression vector shown in FIG. 1. Confirmation of DNA insertion was carried out by determining the base sequence of a DNA sequencer (ABI).

Example 1

Construction of a ZZ-apoAQ Fusion Protein Expression Vector (pCold-ZZ-AQ)

The ZZ gene and aequorin gene were prepared by the following methods in order to express a recombinant ZZ-apoAQ fusion protein in *E. coli*. The ZZ gene, which encodes the ZZ domain (an IgG binding domain), was prepared by PCR from pEZZ18 (Amersham Biosciences). The apoaequorin-encoding aequorin gene was prepared by PCR from pAM-HE containing a HindIII-EcoRI fragment that was the coding region of pAQ440 (Japanese Patent Application Laid-open No. S 61-135586). The pCold II vector (Takara Bio Inc.) was used as the expression vector. A ZZ-apoAQ fusion protein expression vector was constructed as follows.

Figure 2:
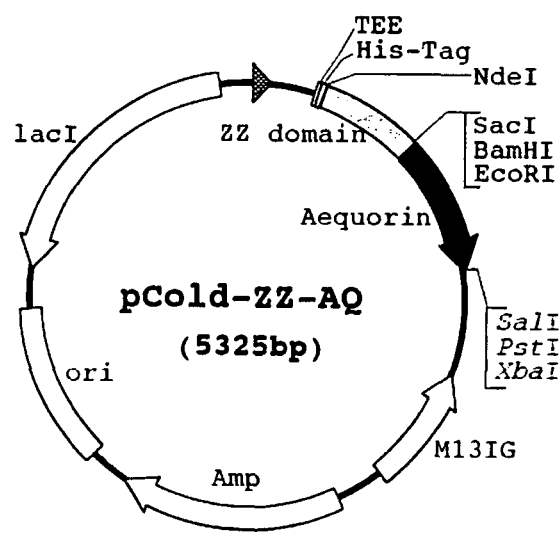
FIG. 2 shows the pCold-ZZ-AQ expression vector obtained in Example 1.

Using pEZZ18 as the template and the two PCR primers 6ZZ-N-NdeI (5' CCG CATATG GCG CAA CAC GAT GAA GCC GTG 3' (SEQ ID NO: 29); the NdeI restriction enzyme site is underlined) and 7ZZ-C-BamHI (5' GGC GGATCC CGA GCT CGA ATT TGC GTC TAC 3' (SEQ ID NO: 30); the BamHI restriction enzyme site is underlined), the desired DNA region was amplified by PCR (25 cycles, cycle conditions: 1 minute/94° C., 1 minute/50° C., 1 minute/72° C.) using a PCR kit (Takara Bio Inc.). The obtained DNA fragments were purified with a PCR purification kit (Qiagen). The purified DNA fragments were digested by the usual method with the restriction enzymes NdeI/BamHI and were thereafter ligated into the NdeI/BamHI restriction enzyme sites of the pCold-AQ obtained in Reference Example 1 to construct the pCold-ZZ-AQ expression vector shown in FIG. 2. This expression vector was low-temperature inducible. The expressed ZZ-apoAQ had a histidine tag at its amino terminus.

Reference Example 2

Construction of an hGL Expression Vector (pCold-hGL)

In order to express the *Gaussia* luciferase protein, originating from the deep-sea copepod *Gaussia princes*, in *E. coli*, the *Gaussia* luciferase gene (hGL gene) was prepared from pcDNA3-hGL (LUX biotechnology ltd.), which contained the *Gaussia* luciferase gene. As the expression vector, pCold II was used (Takara Bio Inc.).

Figure 3:
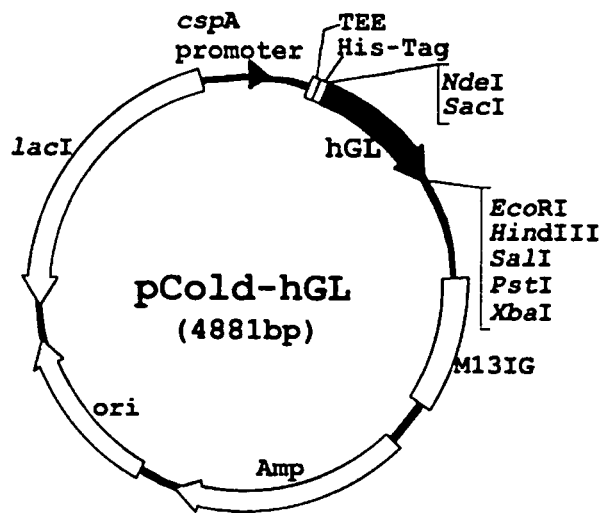
FIG. 3 shows the pCold-hGL expression vector obtained in Reference Example 2.

Using the *Gaussia* luciferase gene-containing pcDNA3-hGL (LUX biotechnology ltd.) as the template and the two PCR primers GL5-N/SacI (5' gcc GAGCTC AAG CCC ACC GAG AAC AAC GAA 3' (SEQ ID NO: 31); the SacI restriction enzyme site is underlined) and GL2-C/EcoRI (5' gcc GAATTC TTA GTC ACC ACC GGC CCC CTT 3' (SEQ ID NO: 32); the EcoRI restriction enzyme site is underlined), the desired DNA region was amplified by PCR (25 cycles, cycle conditions: 1 minute/94° C., 1 minute/50° C., 1 minute/72° C.) using a PCR kit (Takara Bio Inc.). The obtained fragments were purified with a PCR purification kit (Qiagen), digested by the usual method with the restriction enzymes SacI/EcoRI, and thereafter ligated into the SacI/EcoRI restriction enzyme sites of pCold II to construct the pCold-hGL expression vector shown in FIG. 3.

Example 2

Construction of a ZZ-hGL Expression Vector (pCold-ZZ-hGL)

The ZZ gene and *Gaussia* luciferase gene were prepared by the following methods in order to express a recombinant ZZ-hGL fusion protein in *E. coli*. The ZZ gene, which encodes the ZZ domain (an IgG binding domain), was prepared by PCR from the ZZ gene-carrying pEZZ18 (Amersham Biosciences). The *Gaussia* luciferase gene (hGL gene) was prepared by PCR from the *Gaussia* luciferase gene-containing pcDNA3-hGL (LUX biotechnology ltd.). pCold II (Takara Bio Inc.) was used as the expression vector.

Figure 4:
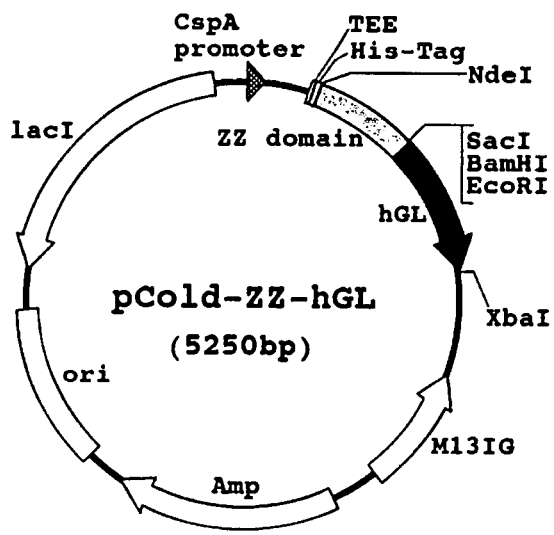
FIG. 4 shows the pCold-ZZ-hGL expression vector obtained in Example 2.

Using pcDNA3-hGL as the template and the two PCR primers GL6-N/EcoRI (5' gcc GAATTC AAG CCC ACC GAG AAC AAC GAA 3' (SEQ ID NO: 33); the EcoRI restriction enzyme site is underlined) and GL-C/XbaI (5' gcc TCTAGA TTA GTC ACC ACC GGC CCC CTT 3' (SEQ ID NO: 34); the XbaI restriction enzyme site is underlined), the desired DNA region was amplified by PCR (25 cycles, cycle conditions: 1 minute/94° C., 1 minute/50° C., 1 minute/72° C.) using a PCR kit (Takara Bio Inc.). The obtained fragments were purified with a PCR purification kit (Qiagen), digested by the usual method with the restriction enzymes EcoRI/XbaI, and thereafter ligated into the EcoRI/XbaI restriction enzyme sites of pCold-ZZ-AQ to construct the pCold-ZZ-hGL expression vector shown in FIG. 4.

Reference Example 3

Construction of a KAZ Expression Vector (pCold-KAZ)

In order to express in *E. coli* the 19 kDa protein (KAZ) that is the catalytic unit of the *Oplophorus* (shrimp) luciferase originating from the deep-sea shrimp *Oplophorus gracilirostris*, the gene coding for the 19 kDa protein (KAZ gene) was prepared from pHis-KAZ (Inouye et al., *FEBS Lett.*, 481, 19-25 (2000)). pCold II (Takara Bio Inc.) was used as the expression vector.

Figure 5:
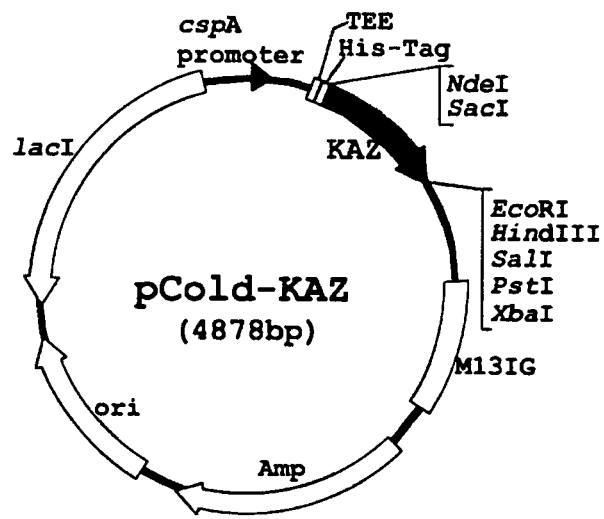
FIG. 5 shows the pCold-KAZ expression vector obtained in Reference Example 3.

Using pHis-KAZ as the template and the two PCR primers KAZ-17N/NdeI (5' gcg CATATG TTT ACG TTG GCA GAT TTC GTT 3' (SEQ ID NO: 35); the NdeI restriction enzyme site is underlined) and KAZ-12C/EcoRI (5' cgc GAATTC TTA GGC AAG AAT GTT CTC GCA AAG CCT 3' (SEQ ID NO: 36); the EcoRI restriction enzyme site is underlined), the desired DNA region was amplified by PCR (25 cycles, cycle conditions: 1 minute/94° C., 1 minute/50° C., 1 minute/72° C.) using a PCR kit (Takara Bio Inc.). The obtained fragments were purified with a PCR purification kit (Qiagen), digested by the usual method with the restriction enzymes NdeI/EcoRI, and thereafter ligated into the NdeI/EcoRI restriction enzyme sites of pCold II to construct the pCold-KAZ expression vector shown in FIG. 5.

Example 3

Construction of a ZZ-KAZ Expression Vector (pCold-ZZ-KAZ)

The ZZ gene and KAZ gene were prepared by the following methods in order to express a recombinant ZZ-KAZ fusion protein in *E. coli*. The ZZ gene, which encodes the ZZ domain (an IgG binding domain), was prepared by PCR from the ZZ gene-carrying pEZZ18 (Amersham Biosciences). The luciferase gene of *Oplophorus* (shrimp) origin was prepared by PCR from pHis-KAZ (Inouye et al., *FEBS Lett.*, 481, 19-25 (2000)), which carried the *Oplophorus* (shrimp) luciferase gene. The pCold II expression vector (Takara Bio Inc.) was used as the expression vector.

Figure 6:
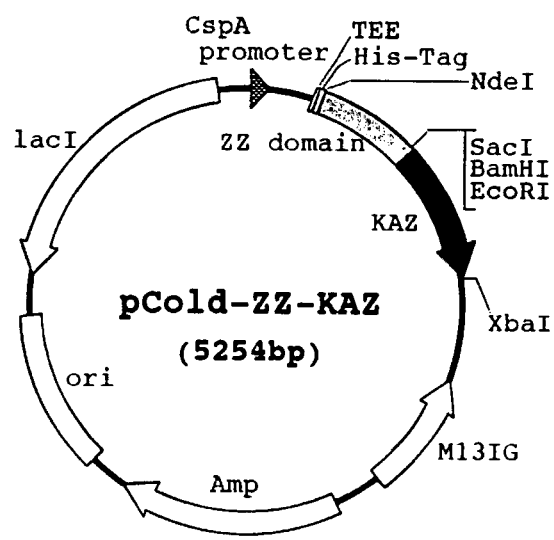
FIG. 6 shows the pCold-ZZ-KAZ expression vector obtained in Example 3.

Using pHis-KAZ-NX as the template and the two PCR primers KAZ-8N/EcoRI (5' gcg GAATTC TTT ACG TTG GCA GAT TTC GTT GGA 3' (SEQ ID NO: 37); the EcoRI restriction enzyme site is underlined) and KAZ-5C/XbaI (5' cc gcTCTAGAA TTA GGC AAG AAT GTT CTC GCA AAG-CCT 3' (SEQ ID NO: 38); the XbaI restriction enzyme site is underlined), the desired DNA region was amplified by PCR (25 cycles, cycle conditions: 1 minute/94° C., 1 minute/50° C., 1 minute/72° C.) using a PCR kit (Takara Bio Inc.). The obtained fragments were purified with a PCR purification kit (Qiagen), digested by the usual method with the restriction enzymes EcoRI/XbaI, and thereafter ligated into the EcoRI/XbaI restriction enzyme sites of pCold-ZZ-AQ to construct the pCold-ZZ-KAZ expression vector shown in FIG. 6.

Example 4

Construction of the pCold-ZZ-T-hGL and pCold-ZZ-P-hGL Expression Vectors

In order to excise the ZZ protein moiety from the ZZ-fused hGL protein referenced in Example 2, two vectors, pCold-ZZ-T-hGL and pCold-ZZ-P-hGL, each having a thrombin cleavage site or a human rhinovirus 3C protease cleavage site in the fusion region, were constructed as follows.

Figure 7:
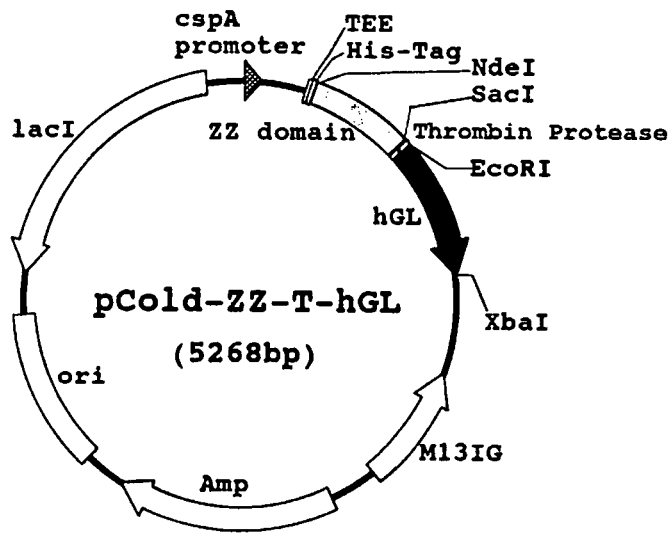
FIG. 7 shows the pCold-ZZ-T-hGL expression vector obtained in Example 4.
Figure 8:
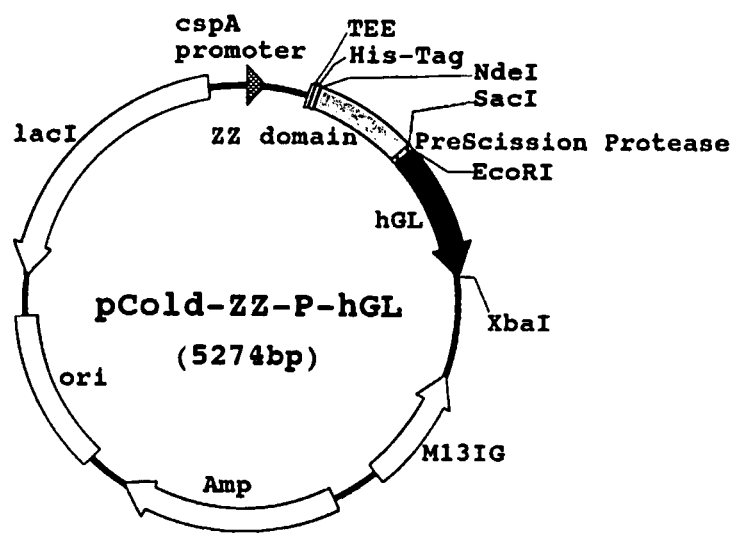
FIG. 8 shows the pCold-ZZ-P-hGL expression vector obtained in Example 4.

The pCold-ZZ-hGL obtained in Example 2 was digested with the restriction enzymes BamHI/EcoRI and the oligonucleotides corresponding to the protease cleavage site sequence was synthesized and inserted. Thrombin B/E-F 5' GA TCT CTG GTT CCG CGT GGA TCC G 3' (SEQ ID NO: 39) and Thrombin B/E-R 5' AA TTC GGA TCC ACG CGG AAC CAG A 3' (SEQ ID NO: 40) were used as the thrombin cleavage recognition sequence oligonucleotides. PreScission B/E-F 5' GA TCT CTG GAA GTT CTG TTC CAG GGG CCC G 3' (SEQ ID NO: 41) and PreScission B/E-R 5' AA TTC GGG CCC CTG GAA CAG AAC TTC CAG A 3' (SEQ ID NO: 42) were used as the human rhinovirus 3C protease cleavage recognition sequence oligonucleotides. These oligonucleotides were annealed and inserted by the usual method via the BamHI/EcoRI of the pCold-ZZ-hGL expression vector obtained in Example 2 to construct the pCold-ZZ-T-hGL expression vector shown in FIG. 7 and the pCold-ZZ-P-hGL expression vector shown in FIG. 8.

Example 5

Production of Recombinant ZZ-apoAQ Fusion Protein

Recombinant ZZ-apoAQ fusion protein was prepared as described below by expressing recombinant ZZ-apoAQ fusion protein in *E. coli*, extracting the expressed fusion protein, and purifying the extracted fusion protein using several chromatographic techniques.

The luminescent activity of the fusion protein was measured during the purification process as follows. Luminescence-capable ZZ-AQ fusion protein was first prepared by mixing crude ZZ-apoAQ fusion protein solution, 2-mercaptoethanol (1 μL), and coelenterazine substrate (1 μg/μL) dissolved in ethanol, in 1 mL of 50 mM Tris-HCl (pH 7.6) buffer solution that contained 10 mM EDTA, followed by standing for 2 hours on ice (4° C.). The luminescence reaction was started by the addition of 100 μL 50 mM $CaCl_2$ to the resulting ZZ-AQ fusion protein solution, and the 10-second luminescence activity was measured with a PSN AB2200 luminometer (ATTO Corporation). The luminescence activity (for example, maximum value (Imax)) was evaluated as the relative luminescence intensity (rlu).

Expression of Recombinant ZZ-apoAQ Fusion Protein in *E. coli*

The pCold-ZZ-AQ expression vector obtained in Example 1 was transfected into *E. coli* strain BL21 by the polyethylene glycol method to give a transformant. This transformant was cultured for 18 hours at 37° C. After cultivation, the transformant was inoculated to 10 mL LB liquid medium (pH 7.2, 10 g bactotryptone, 5 g yeast extract, and 5 g sodium chloride per 1 L water) that contained ampicillin (100 μg/mL) and was then cultured for another 18 hours at 37° C. The obtained bacterial culture fluid was thereafter added to 2 L fresh LB liquid medium (5×400 mL) and cultured for 4.5 hours at 37° C. After culture, the resulting bacterial culture fluid was cooled on ice water and isopropyl-β-D(−)-thiogalactopyranoside (IPTG, Wako Pure Chemical Industries, Ltd.) was added to the culture fluid to a final concentration of 0.1 mM. Culture was again carried out for 17 hours at 15° C. The cultured bacteria were collected using a refrigerated centrifuge at 5,000 rpm (6000×g) for 5 minutes.

Extraction of the ZZ-apoAQ Fusion Protein from the Cultured Bacteria

The bacteria collected in 1) above were suspended in 200 mL (5×40 mL) 50 mM Tris-HCl (pH 7.6) and, while cooling with ice, were subjected to an ultrasonic disruption treatment (3 times, 2 minutes each, Sonifier Model 250 from Branson). The resulting liquid bacterial disruptate was submitted to centrifugal separation for 20 minutes at 10,000 rpm (12,000× g), and the obtained soluble fraction was used as the starting point for purification of the ZZ-apoAQ fusion protein.

Purification of the ZZ-apoAQ Fusion Protein by Q-Sepharose Column Chromatography The soluble fraction (200 mL) obtained in 2) above was added and adsorbed onto a Q-Sepharose column (Amersham Biosciences, column size: diameter 2.5×6 cm) that had been equilibrated with 50 mM Tris-HCl (pH 7.6), and the column was thereafter washed with 250 mL 50 mM Tris-HCl (pH 7.6). The protein adsorbed on the column was eluted with a linear concentration gradient of 0 to 1.0 M sodium chloride using a total volume of 100 mL. Elution of luminescence-capable ZZ-apoAQ fusion protein was confirmed at a sodium chloride concentration of 0.45 to 0.65 M (25 mL, ZZ-apoAQ active fraction).

Purification of ZZ-apoAQ Fusion Protein by Nickel Chelate Column Chromatography

The ZZ-apoAQ active fraction eluted from the Q-Sepharose column was added to a nickel chelate column (Amersham Biosciences, column size: diameter 1.5×5 cm) that had been equilibrated with 50 mM Tris-HCl (pH 7.6) and the ZZ-apoAQ fusion protein was adsorbed thereon. The adsorbed ZZ-apoAQ fusion protein was eluted with a linear concentration gradient of 0 to 0.3 M imidazole (Wako Pure Chemical Industries, Ltd.) using a total volume of 100 mL. Elution of luminescence-capable ZZ-apoAQ fusion protein was confirmed at an imidazole concentration of 0.06 to 0.12 M (26 mL, ZZ-apoAQ active fraction).

Purification of ZZ-apoAQ Fusion Protein by IgG-Sepharose Column Chromatography

A portion of the ZZ-apoAQ active fraction eluted from the nickel chelate column was concentrated using an Amicon Ultra-4 centrifugal filter device (molecular weight cutoff: 10,000, Millipore). The concentrated solution (4 mL) was added to an IgG-Sepharose 6FastFlow column (Amersham Biosciences, column size: diameter 1.5×4 cm) and the ZZ-apoAQ fusion protein was adsorbed thereon. The adsorbed ZZ-apoAQ fusion protein was eluted with 0.5 M ammonium acetate (pH 3.4) (Wako Pure Chemical Industries, Ltd.).

Figure 9:
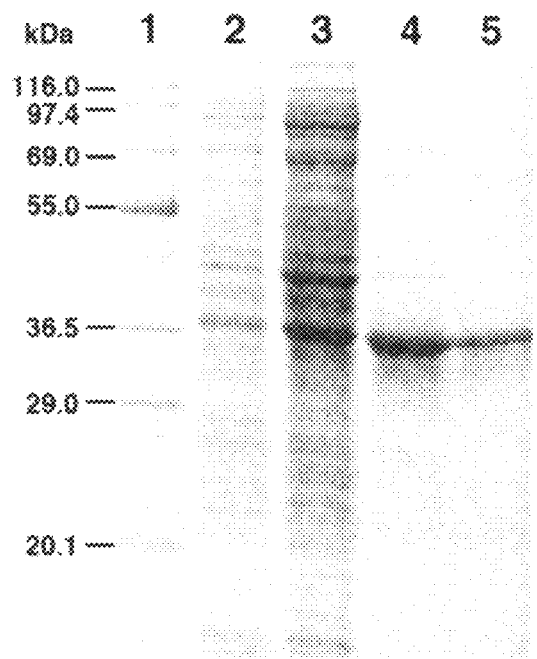
FIG. 9 shows the results of SDS-PAGE analysis during the process of ZZ-apoaequorin purification in Example 5. The substances in the individual lanes are as follows. Lane 1: molecular weight marker proteins (TEFCO): β-galactosidase (116,000), phospholipase B (97,400), bovine serum albumin (69,000), glutamate dehydrogenase (55,000), lactate dehydrogenase (36,500), carbonic anhydrase (29,000), trypsin inhibitor (20,100). Lane 2: supernatant (5.4 μg protein) obtained by centrifugation at 12,000 g of the ultrasonicate of the *E. coli* transformant that expressed recombinant ZZ-apoAQ. Lane 3: eluted fraction (16 μg protein) from the Q-Sepharose column. Lane 4: eluted fraction (4.8 μg protein) from the nickel chelate column. Lane 5: eluted fraction (1.3 μg protein) from the IgG-Sepharose column.

As shown in FIG. 9, the purity was confirmed by 12% SDS-polyacrylamide electrophoresis to be at least 95%.

The purification yields were as shown in Table 1. The IgG-Sepharose column yielded 7.8 mg purified ZZ-apoAQ with a purity of at least 95%, from the equivalent of 420 mL culture liquid.

was added, and conversion to the ZZ-AQ fusion protein was achieved by holding for 24 hours at 4° C. The obtained ZZ-AQ fusion protein was concentrated with an Amicon Ultra-4 (molecular weight cutoff: 10,000) and then washed with 8 mL (2 mL four times) 50 mM Tris-HCl (pH 7.6) including 10 mM EDTA to remove the excess coelenterazine. ZZ-AQ fusion protein was obtained at an activity recovery rate of 95%.

Example 7

Measurement of the Luminescence Activity of the Recombinant Proteins

Expression of Recombinant Proteins by *E. coli*

A transformant was obtained by transfecting a ZZ fusion protein expression vector (pCold-ZZ-AQ, pCold-ZZ-hGL, pCold-ZZ-KAZ) or a non-ZZ fusion protein expression vector (pCold-AQ, pCold-hGL, pCold-KAZ) into the *E. coli* host strain BL21 using the polyethylene glycol method. The resulting transformant was inoculated to 10 mL LB liquid medium (pH 7.2, 10 g bactotryptone, 5 g yeast extract, and 5 g sodium chloride per 1 L water) (the same LB liquid medium was used in all of the cultivations hereafter referenced in this example) that included ampicillin (100 μg/mL) and was then cultured for another 18 hours at 37° C. The obtained bacterial culture fluid was then added to 10 mL fresh LB liquid medium and cultured for 4.5 hours at 37° C. After culture, the resulting culture fluid was cooled on ice water and isopropyl-β-D-(−)-thiogalactopyranoside (IPTG, Wako Pure Chemical Industries, Ltd.) was added to the culture fluid to a final concentration of 0.1 mM. Culture was again carried out for 17 hours at 15° C. 1 mL of cultured bacteria was collected using a refrigerated centrifuge at 5,000 rpm (6000×g) for 5 minutes.

Extraction of the Recombinant Protein from the Cultured Bacteria

The collected bacteria were suspended in 1 mL 50 mM Tris-HCl (pH 7.6) including 10 mM EDTA and, while cooling with ice, were subjected to an ultrasonic disruption treatment (Sonifier Model 250 from Branson) for 30 seconds. The

TABLE 1

| purification process | total quantity (mL) | protein concentration (mg/mL) | total amount of protein (mg) | activity ($\times 10^{11}$ rlu/mL) | specific activity ($\times 10^{10}$ rlu/mg) | total activity ($\times 10^{12}$ rlu) | yield (%) | purification factor |
|---|---|---|---|---|---|---|---|---|
| supernatant from the ultrasonicate (12,000 × g) | 200 | 2.7 | 540 | 0.36 | 1.33 | 7.20 | 100 | 1.00 |
| Q-Sepharose FF column | 25 | 8.0 | 200 | 2.34 | 2.93 | 5.85 | 82.9 | 2.20 |
| Ni chelate FF column | 26 | 1.75 | 45.5 | 1.82 | 10.40 | 4.73 | 67.1 | 7.82 |
| Ni chelate FF column | 4 | 2.40 | 9.6 | 2.50 | 10.42 | 1.00 | 100 | 78.3 |
| IgG-Sepharose 6FF column | 10 | 0.78 | 7.8 | 1.03 | 13.21 | 1.03 | 103 | 9.93 |

Example 6

Preparation of ZZ-AQ Fusion Protein

Conversion from the ZZ-apoAQ fusion protein to the ZZ-AQ fusion protein was carried out under the following conditions.

The purified ZZ-apoAQ fusion protein (1 mg) obtained in Example 5 was dissolved in 5 mL 50 mM Tris-HCl (pH 7.6) containing 10 mM DTT and 10 mM EDTA, 24 μg coelenterazine (1.2-fold on an equivalents basis) dissolved in ethanol resulting liquid bacterial disruptate was submitted to centrifugal separation for 3 minutes at 10,000 rpm (12,000×g) and the supernatant was used as the soluble fraction. The precipitate was then suspended in 1 mL 50 mM Tris-HCl (pH 7.6) including 10 mM EDTA and this was used as the insoluble fraction.

Measurement of the Luminescence Activity of the Luminescent Protein Aequorin

Luminescence-capable aequorin was regenerated by dissolving 50 μL of the soluble fraction or insoluble fraction obtained in (2) above in 0.95 mL 50 mM Tris-HCl (pH 7.6) that included 10 mM EDTA; mixing 2-mercaptoethanol (1

μL) and coelenterazine substrate (1 μg/μL) dissolved in ethanol and thereafter adding the apoaequorin fraction; and holding for 2 hours on ice (4° C.). The luminescence reaction was started by the addition of 100 μL CaCl$_2$ to 1 μL of the regenerated aequorin, and the 10-second luminescence activity was measured with a Luminescencer-PSN AB2200 luminometer (ATTO Corporation). This measurement of the luminescence activity was carried out three times, and the luminescence activity was evaluated as the average (rlu) of the maximum value (Imax) of the luminescence activity.

Measurement of the Luminescence Activity of *Oplophorus* (Shrimp) Luciferase

1 μL of the soluble fraction or insoluble fraction obtained in (2) above was dissolved in 0.1 mL 50 mM Tris-HCl (pH 7.6) that included 10 mM EDTA; the luminescence reaction was started by the admixture of coelenterazine substrate (1 μg/μL) dissolved in ethanol; and the 60-second luminescence activity was measured with a Luminescencer-PSN AB2200 luminometer (ATTO Corporation). This measurement of the luminescence activity was carried out three times, and the luminescence activity was evaluated as the average (rlu) of the maximum value (Imax) of the luminescence activity.

Measurement of the Luminescence Activity of *Gaussia* Luciferase

1 μL of the soluble fraction or insoluble fraction obtained in (2) above was dissolved in 0.1 mL 50 mM Tris-HCl (pH 7.6) that included 10 mM EDTA; the luminescence reaction was started by the admixture of coelenterazine substrate (1 μg/μL) dissolved in ethanol; and the 60-second luminescence activity was measured with a Luminescencer-PSN AB2200 luminometer (ATTO Corporation). This measurement of the luminescence activity was carried out three times, and the luminescence activity was evaluated as the average (rlu) of the maximum value (Imax) of the luminescence activity.

The results are shown in Table 2. The solubility rate is clearly higher for expression as the ZZ fusion protein when heterologous protein is expressed in *E. coli*.

TABLE 2

| expression vector | fraction | luminescence activity (Imax, rlu) | relative activity (%) |
| --- | --- | --- | --- |
| pCold-AQ | soluble fraction (S) | 25942 | 9.2 |
|  | insoluble fraction (P) | 95308 | 33.8 |
| pCold-ZZ-AQ | soluble fraction (S) | 281976 | 100 |
|  | insoluble fraction (P) | 25096 | 8.9 |
| pCold-hGL | soluble fraction (S) | 116505 | 29.4 |
|  | insoluble fraction (P) | 14266 | 3.6 |
| pCold-ZZ-hGL | soluble fraction (S) | 396275 | 100 |
|  | insoluble fraction (P) | 17040 | 4.3 |
| pCold-KAZ | soluble fraction (S) | 6444 | 4.7 |
|  | insoluble fraction (P) | 3702 | 2.7 |
| pCold-ZZ-KAZ | soluble fraction (S) | 137106 | 100 |
|  | insoluble fraction (P) | 137 | 0.1 |

A cysteine residue is present at three locations in the molecule in apoaequorin (apoAQ). Apoaequorin is expressed as an insoluble protein when expression in *E. coli* is carried out at the usual temperature (37° C.). This requires the use of a denaturant for solubilization. However, when expression as the ZZ fusion protein was carried out, the ZZ-apoAQ was soluble and it was possible to carry out conversion (regeneration) to luminescence-capable aequorin. In addition, with regard to the insoluble fraction of pCold-AQ, a little over a 30% regeneration to aequorin was possible in the absence of a denaturant in the case of low-temperature expression.

A cysteine residue is present at ten locations in the molecule in *Gaussia* luciferase (hGL). It is known for natural *Gaussia* luciferase that its luminescence activity is completely deactivated by treatment with a reducing agent. In addition, it is known that *Gaussia* luciferase has a poor refolding efficiency in *E. coli*. It was shown, however, that expression as the ZZ fusion protein increases the refolding efficiency approximately 5-fold with respect to that for the non-ZZ fusion protein expression system. In addition, there was also an indication that this is a case where the refolding efficiency is boosted by low-temperature cultivation.

When *Oplophorus* (shrimp) luciferase (KAZ) is expressed in *E. coli*, it is expressed as insoluble protein, as has already been reported (Inouye et al., *FEBS Lett.* 2000:481, 19-25), and the crude extract from *E. coli* has an extremely low activity. However, when KAZ was expressed as a ZZ fusion protein, it was shown to be soluble and to have luminescence activity.

Example 8

SDS-PAGE Analysis of Recombinant Proteins

Expression of Recombinant Proteins by *E. coli*

A transformant was obtained by transfecting a ZZ fusion protein expression vector (pCold-ZZ-AQ, pCold-ZZ-hGL, pCold-ZZ-KAZ, pCold-ZZ-T-hGL, pCold-ZZ-P-hGL)) or a non-ZZ fusion protein expression vector (pCold-AQ, pCold-hGL, pCold-KAZ) into the *E. coli* host strain BL21 using the polyethylene glycol method. The resulting transformant was inoculated to 10 mL LB liquid medium (pH 7.2, 10 g bactotryptone, 5 g yeast extract, and 5 g sodium chloride per 1 L water) that contained ampicillin (100 μg/mL) and was then cultured for another 18 hours at 37° C. The 0.1 mL of the obtained bacterial culture fluid was then added to 10 mL fresh LB liquid medium and cultured for 4.5 hours at 37° C. After culture, the resulting culture fluid was cooled on ice water and isopropyl-β-D(−)-thiogalactopyranoside (IPTG, Wako Pure Chemical Industries, Ltd.) was added to the culture fluid to a final concentration of 0.1 mM. Culture was again carried out for 17 hours at 15° C. 1 mL of the cultured bacteria was collected using a refrigerated centrifuge at 5,000 rpm (6000× g) for 5 minutes.

Extraction of the Recombinant Protein from the Cultured Bacteria

The collected bacteria were suspended in 0.5 mL 50 mM Tris-HCl (pH 7.6) including 10 mM EDTA and, while cooling with ice, were subjected to an ultrasonic disruption treatment (Sonifier Model 250 from Branson) for 30 seconds. The resulting liquid bacterial disruptate was submitted to centrifugal separation for 3 minutes at 10,000 rpm (12,000×g) and the supernatant was used as the soluble fraction (S). The precipitate was then suspended in 0.5 mL 50 mM Tris-HCl (pH 7.6) including 10 mM EDTA and this was used as the insoluble fraction (P).

SDS-PAGE Analysis of the Recombinant Proteins

Figure 10:
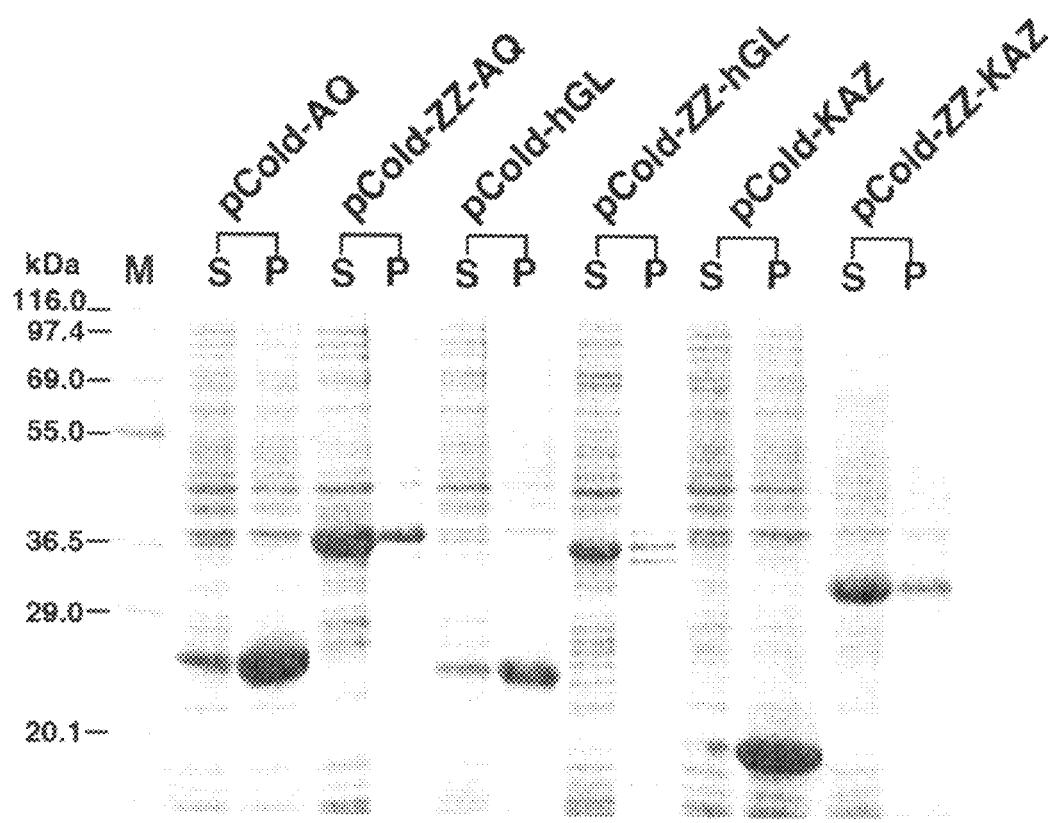
FIG. 10 shows the results of SDS-PAGE analysis in Example 8. In the figure, M refers to the following protein molecular weight markers (TEFCO): β-galactosidase (116,000), phospholipase B (97,400), bovine serum albumin (69,000), glutamate dehydrogenase (55,000), lactate dehydrogenase (36,500), carbonic anhydrase (29,000), trypsin inhibitor (20,100). S refers to the soluble supernatant fraction and P refers to the insoluble precipitate fraction that were obtained when the ultrasonicate of an *E. coli* transformant that had expressed the expression plasmid was subjected to centrifugation for 3 minutes at 12,000 g.

20 μL Laemmli sample buffer was added to 20 μL of the soluble fraction or insoluble fraction obtained in (2) above followed by treatment for 3 minutes at 95° C., loading onto a 12% (w/v) SDS-PAGE gel (TEFCO), and electrophoresis for 90 minutes at 25 mA. After phoresis, the gel was treated for 30 minutes with a fixing solution (methanol:acetic acid:water=50 mL:10 mL:40 mL), followed by staining for 1 hour with a colloid CBB stain kit (TEFCO). Destaining was carried out by washing with 200 mL distilled water. The results are shown in FIG. 10. In the case of the non-ZZ fusion protein expression vector systems pCold-AQ, pCold-hGL, and pCold-KAZ, their expressed protein was observed mainly in the insoluble fraction (P). In contrast, in the case of the ZZ fusion protein expression vector systems pCold-ZZ-AQ, pCold-ZZ-hGL, pCold-ZZ-KAZ, their expressed protein was observed mainly in the soluble fraction (S). This result also correlated with the luminescence activity, and the luminescence activity was higher in the case of expression as the ZZ fusion protein than for expression as the non-ZZ fusion protein.

These results showed that an activity-capable protein can be efficiently expressed as soluble protein by fusion with ZZ protein.

Figure 11:
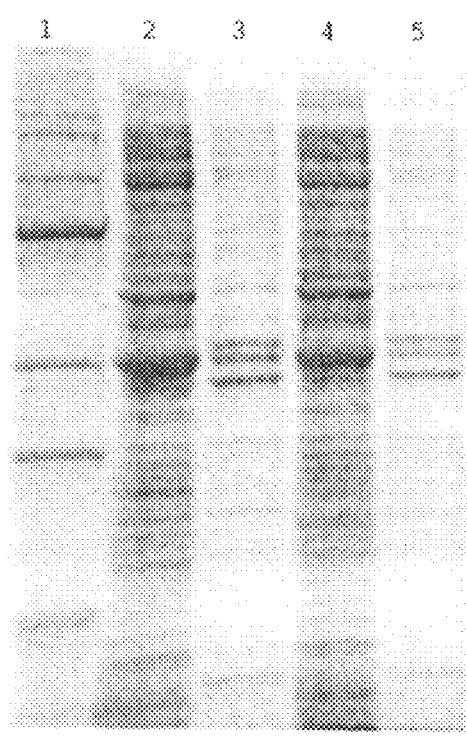
FIG. 11 shows the results of SDS-PAGE analysis in Example 8. The substances in the individual lanes are as follows. Lane 1: molecular weight marker proteins (TEFCO): β-galactosidase (116,000), phospholipase B (97,400), bovine serum albumin (69,000), glutamate dehydrogenase (55,000), lactate dehydrogenase (36,500), carbonic anhydrase (29,000), trypsin inhibitor (20,100). Lane 2: supernatant (soluble fraction (S)) obtained when the ultrasonicate of an *E. coli* transformant that had expressed recombinant ZZ-P-hGL was subjected to centrifugation for 3 minutes at 12,000 g. Lane 3: precipitate (insoluble fraction (P)) obtained when the ultrasonicate of an *E. coli* transformant that had expressed recombinant ZZ-P-hGL was subjected to centrifugation for 3 minutes at 12,000 g. Lane 4: supernatant (soluble fraction (S)) obtained when the ultrasonicate of an *E. coli* transformant that had expressed recombinant ZZ-T-hGL was subjected to centrifugation for 3 minutes at 12,000 g. Lane 5: precipitate (insoluble fraction (P)) obtained when the ultrasonicate of an *E. coli* transformant that had expressed recombinant ZZ-T-hGL was subjected to centrifugation for 3 minutes at 12,000 g.

As shown in FIG. 11, it was also demonstrated that expression using the pCold-ZZ-T-hGL and pCold-ZZ-P-hGL vectors, which each had a protease cleavage recognition site, likewise made it possible to efficiently express an activity-capable protein as soluble protein.

INDUSTRIAL APPLICABILITY

The expression vector of the invention and the method of the invention for producing a target protein, because they enable the production of the target protein as a soluble protein, make it unnecessary to solubilize the target protein. As a consequence the invention enables a target protein to be obtained efficiently and at high recovery rates. The invention is therefore useful for the production of protein, for example, useful protein, protein that is the subject of an analysis of structure and/or function, and so forth.

The expression vector of the invention that contains at least one restriction enzyme site enables the production of a target protein as a soluble protein through the insertion of a gene coding for the target protein into the restriction site and the expression of same. This expression vector can therefore be very suitably used for the production of a target protein, for example, a useful protein.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. An expression vector for expression of a fusion protein, comprising:
   (1) an expression-inducible promoter sequence, wherein the expression-inducible promoter sequence is a cold-shock promoter sequence selected from the group consisting of a cspA promoter sequence, a cspB promoter sequence, a cspG promoter sequence, a cspI promoter sequence, and a csdA promoter sequence;
   (2) a first coding sequence comprising a polynucleotide encoding a polypeptide that is represented by the formula $(Z)_n$,
   wherein n represents an integer from 1 to 5 and Z represents polypeptide selected from the group of:
      (a) a polypeptide comprising the amino acid sequence of SEQ ID NO: 1,
      (b) a polypeptide comprising an amino acid sequence that has at least 95% identity with the amino acid sequence of SEQ ID NO: 1, and
      (c) a polypeptide comprising an amino acid sequence that has at least 98% identity with the amino acid sequence of SEQ ID NO: 1, and
   that has the capacity when expressed as a fusion protein with a target protein to render said fusion protein expressible as a soluble protein; and
   (3) a second coding sequence that comprises a polynucleotide that encodes a target protein,
   wherein the vector further comprises, on the 5' side of the first coding sequence, a coding sequence that comprises a polynucleotide that encodes an amino acid sequence that facilitates purification, and
   wherein the expression of the fusion protein comprising the amino acid sequence that facilitates purification, the amino acid sequence of the polypeptide that is represented by the formula $(Z)_n$ and the amino acid sequence of the target protein is induced in *Escherichia coli*, and the fusion protein accumulates within the *Escherichia coli* as a soluble protein so that the fusion protein collected from within the *Escherichia coli* has higher solubility rate than non-$(Z)n$ fusion protein.

2. The vector according to claim 1, wherein the polypeptide represented by formula $(Z)_n$ is a polypeptide represented by $(Z)_2$.

3. The vector according to claim 2, wherein the polypeptide represented by $(Z)_2$ is a polypeptide selected from the group of
   (d) a polypeptide comprising the amino acid sequence of SEQ ID NO: 3,
   (e) a polypeptide that comprises an amino acid sequence having at least 95% identity with the amino acid sequence of SEQ ID NO: 3, and that has the capacity when expressed as a fusion protein with a target protein to render said fusion protein expressible as a soluble protein, and
   (f) a polypeptide that comprises an amino acid sequence having at least 98% identity with the amino acid sequence of SEQ ID NO: 3, and that has the capacity when expressed as a fusion protein with a target protein to render said fusion protein expressible as a soluble protein.

4. The vector according to claim 1, further comprising, between the first coding sequence and the second coding sequence, a coding sequence comprising a polynucleotide encoding a cleavable linker peptide.

5. The vector according to claim 4, wherein the cleavable linker peptide is a linker peptide having a protease cleavage site.

6. The vector according to claim 1, wherein the amino acid sequence that facilitates the purification is a histidine tag sequence.

7. The expression vector according to claim 1, wherein the target protein is an apoprotein of a holoprotein.

8. The expression vector according to claim 1, wherein the target protein is *Gaussia* luciferase (hGL) or 19 kDa protein that is the catalytic unit of *Oplophorus* (shrimp) luciferase (KAZ).

9. The expression vector according to claim 1, wherein a temperature for the expression induction is 10 to 20° C.

10. An expression vector for expression of a fusion protein, comprising:
   (1) an expression-inducible promoter sequence, wherein the expression-inducible promoter sequence is a cold-shock promoter sequence selected from the group consisting of a cspA promoter sequence, a cspB promoter sequence, a cspG promoter sequence, a cspI promoter sequence, and a csdA promoter sequence;
   (2) a first coding sequence comprising a polynucleotide encoding a polypeptide that is represented by the formula $(Z)n$, wherein n represents an integer from 1 to 5 and Z represents polypeptide selected from the group of:
      (a) a polypeptide comprising the amino acid sequence of SEQ ID NO: 1,
      (b) a polypeptide comprising an amino acid sequence that has at least 95% identity with the amino acid sequence of SEQ ID NO: 1, and
      (c) a polypeptide comprising an amino acid sequence that has at least 98% identity with the amino acid sequence of SEQ ID NO: 1, and
   that has the capacity when expressed as a fusion protein with a target protein to render said fusion protein expressible as a soluble protein; and
   (3) at least one restriction enzyme site that enables the insertion of a second coding sequence that comprises a polynucleotide that encodes a target protein,
   wherein the vector further comprises, on the 5' side of the first coding sequence, a coding sequence that comprises a polynucleotide that encodes an amino acid sequence that facilitates purification, and
   wherein the expression of the fusion protein comprising the amino acid sequence that facilitates purification, the amino acid sequence of the polypeptide that is represented by the formula $(Z)n$ and the amino acid sequence of the target protein is induced in *Escherichia coli*, and the fusion protein accumulates within the *Escherichia coli* as a soluble protein so that the fusion protein collected from within the *Escherichia coli* has higher solubility rate than non-(Z)n fusion protein.

11. The vector according to claim 10, wherein the polypeptide represented by formula $(Z)_n$ is a polypeptide represented by $(Z)_2$.

12. The vector according to claim 11, wherein the polypeptide represented by $(Z)_2$ is a polypeptide selected from the group of
  (d) a polypeptide comprising the amino acid sequence of SEQ ID NO: 3,
  (e) a polypeptide that comprises an amino acid sequence having at least 95% identity with the amino acid sequence of SEQ ID NO: 3, and that has the capacity when expressed as a fusion protein with a target protein to render said fusion protein expressible as a soluble protein, and
  (f) a polypeptide that comprises an amino acid sequence having at least 98% identity with the amino acid sequence of SEQ ID NO: 3, and that has the capacity when expressed as a fusion protein with a target protein to render said fusion protein expressible as a soluble protein.

13. The vector according to claim 10, further comprising, between the first coding sequence and the second coding sequence, a coding sequence comprising a polynucleotide encoding a cleavable linker peptide.

14. The vector according to claim 13, wherein the cleavable linker peptide is a linker peptide having a protease cleavage site.

15. The vector according to claim 10, wherein the amino acid sequence that facilitates the purification is a histidine tag sequence.

16. The expression vector according to claim 10, wherein the target protein is an apoprotein of a holoprotein.

17. The expression vector according to claim 10, wherein the target protein is *Gaussia* luciferase (hGL) or 19 kDa protein that is the catalytic unit of *Oplophorus* (shrimp) luciferase (KAZ).

18. The expression vector according to claim 10, wherein a temperature for the expression induction is 10 to 20° C.

19. A polynucleotide for expression of a fusion protein comprising
  an expression-inducible promoter sequence, wherein the expression-inducible promoter sequence is a cold-shock promoter sequence selected from the group consisting of a cspA promoter sequence, a cspB promoter sequence, a cspG promoter sequence, a cspI promoter sequence, and a csdA promoter sequence, and
  a polynucleotide that encodes the fusion protein that can be expressed as a soluble protein, comprising:
  (1) a first amino acid sequence comprising the amino acid sequence of a polypeptide that is represented by the formula $(Z)_n$,
  wherein n represents an integer from 1 to 5 and Z represents polypeptide selected from the group of:
    (a) a polypeptide comprising the amino acid sequence of SEQ ID NO: 1,
    (b) a polypeptide comprising an amino acid sequence that has at least 95% identity with the amino acid sequence of SEQ ID NO: 1, and
    (c) a polypeptide comprising an amino acid sequence that has at least 98% identity with the amino acid sequence of SEQ ID NO: 1, and
    that has the capacity when expressed as a fusion protein with a target protein to render said fusion protein expressible as a soluble protein; and
  (2) a second amino acid sequence comprising the amino acid sequence of a target protein, wherein the polynucleotide further comprises, on the 5' side of the first coding sequence, a coding sequence that comprises a polynucleotide that encodes an amino acid sequence that facilitates purification,
  wherein an expression for the polynucleotide which encodes the fusion protein comprising the amino acid sequence that facilitates purification, the amino acid sequence of the polypeptide that is represented by the formula (Z)n and the amino acid sequence of the target protein is induced in *Escherichia coli*, and the fusion protein accumulates within the *Escherichia coli* as a soluble protein so that the fusion protein collected from within the *Escherichia coli* has higher solubility rate than non-(Z)n fusion protein.

20. The polynucleotide according to claim 19, that is DNA.

21. The polynucleotide according to claim 19, wherein the target protein is an apoprotein of a holoprotein.

22. The polynucleotide according to claim 19, wherein the target protein is *Gaussia* luciferase (hGL) or 19 kKa protein that is the catalytic unit of *Oplophorus* (shrimp) luciferase (KAZ).

23. The polynucleotide according to claim 19, wherein a temperature for the expression induction is 10 to 20° C.

24. A method of producing a target protein as a soluble protein, wherein the method comprises: expressing a fusion protein by providing the expression vector according to claim 1.

25. The method according to claim 24, wherein the polypeptide represented by formula $(Z)_n$ is a polypeptide represented by $(Z)_2$.

26. The method according to claim 25, wherein the polypeptide represented by the formula $(Z)_2$ is a polypeptide selected from the group of
  (d) a polypeptide comprising the amino acid sequence of SEQ ID NO: 3,
  (e) a polypeptide that comprises an amino acid sequence having at least 95% identity with the amino acid sequence of SEQ ID NO: 3, and that has the capacity when expressed as a fusion protein with a target protein to render said fusion protein expressible as a soluble protein, and
  (f) a polypeptide that comprises an amino acid sequence having at least 98% identity with the amino acid sequence of SEQ ID NO: 3, and that has the capacity when expressed as a fusion protein with a target protein to render said fusion protein expressible as a soluble protein.

27. The method according to claim 24, further comprising, between the first coding sequence and the second coding sequence, a coding sequence comprising a polynucleotide coding for a cleavable linker peptide.

28. The method according to claim 27, wherein the cleavable linker peptide is a linker peptide having a protease cleavage site.

29. The method according to claim 24, wherein the amino acid sequence that facilitates the purification is a histidine tag sequence.

* * * * *